US010028696B2

(12) United States Patent
Toth et al.

(10) Patent No.: US 10,028,696 B2
(45) Date of Patent: Jul. 24, 2018

(54) METHODS AND SYSTEMS FOR EVALUATING THE INTEGRITY OF A UTERINE CAVITY

(71) Applicant: Minerva Surgical, Inc., Redwood City, CA (US)

(72) Inventors: Akos Toth, Cupertino, CA (US); Robin Bek, Campbell, CA (US); Dominique Filloux, Redwood City, CA (US)

(73) Assignee: Minerva Surgical, Inc., Redwood City, CA (US)

( * ) Notice: Subject to any disclaimer, the term of this patent is extended or adjusted under 35 U.S.C. 154(b) by 0 days.

(21) Appl. No.: 15/488,395

(22) Filed: Apr. 14, 2017

(65) Prior Publication Data
US 2017/0215788 A1    Aug. 3, 2017

Related U.S. Application Data

(62) Division of application No. 13/361,089, filed on Jan. 30, 2012, now Pat. No. 9,655,557.
(Continued)

(51) Int. Cl.
*A61B 5/00* (2006.01)
*A61M 13/00* (2006.01)
(Continued)

(52) U.S. Cl.
CPC .......... *A61B 5/4325* (2013.01); *A61B 5/4836* (2013.01); *A61B 18/042* (2013.01);
(Continued)

(58) Field of Classification Search
CPC .......... A61B 5/4325; A61B 2017/4216; A61B 18/042; A61B 18/1485;
(Continued)

(56) References Cited

U.S. PATENT DOCUMENTS 3,948,259 A * 4/1976 Bolduc ................. A61F 6/22
  128/831
4,611,602 A * 9/1986 Bolduc ................. A61B 17/42
  600/560
(Continued)

FOREIGN PATENT DOCUMENTS

| WO | WO-2006021880 A2 | 3/2006 |
| WO | WO-2011060191 A1 | 5/2011 |
| WO | WO-2012106474 A2 | 8/2012 |

OTHER PUBLICATIONS

European Search Report dated Aug. 21, 2017 for European Patent Application No. EP 12742391.1.
(Continued)

*Primary Examiner* — Max Hindenburg
(74) *Attorney, Agent, or Firm* — Wilson Sonsini Goodrich & Rosati

(57) ABSTRACT

Methods, systems and devices for evaluating the integrity of a uterine cavity. A method comprises introducing transcervically a probe into a patient's uterine cavity, providing a flow of a fluid (e.g., $CO_2$) through the probe into the uterine cavity and monitoring the rate of the flow to characterize the uterine cavity as perforated or non-perforated based on a change in the flow rate.

8 Claims, 20 Drawing Sheets

Related U.S. Application Data

(60) Provisional application No. 61/439,788, filed on Feb. 4, 2011.

(51) Int. Cl.
*A61B 18/04* (2006.01)
*A61B 18/14* (2006.01)
*A61B 18/00* (2006.01)

(52) U.S. Cl.
CPC ....... *A61B 18/1485* (2013.01); *A61M 13/003* (2013.01); *A61B 2018/00214* (2013.01); *A61B 2018/00559* (2013.01); *A61B 2018/00577* (2013.01); *A61B 2018/00821* (2013.01); *A61B 2018/147* (2013.01); *A61B 2505/05* (2013.01)

(58) Field of Classification Search
CPC ........... A61B 2018/00559; A61B 2018/00577; A61B 2018/00821; A61B 2018/147
See application file for complete search history.

(56) References Cited

U.S. PATENT DOCUMENTS

| | | | |
|---|---|---|---|
| 4,611,604 A | 9/1986 | Botvidsson et al. |
| 4,650,462 A | 3/1987 | Desatnick et al. |
| 4,979,948 A | 12/1990 | Geddes et al. |
| 5,147,353 A | 9/1992 | Everett |
| 5,191,883 A | 3/1993 | Lennox et al. |
| 5,437,629 A | 8/1995 | Goldrath |
| 5,460,628 A | 10/1995 | Neuwirth et al. |
| 5,549,546 A | 8/1996 | Schneider et al. |
| 5,653,726 A | 8/1997 | Kieturakis |
| 5,769,880 A | 6/1998 | Truckai et al. |
| 5,891,134 A | 4/1999 | Goble et al. |
| 5,925,038 A | 7/1999 | Panescu et al. |
| 5,954,715 A | 9/1999 | Harrington et al. |
| 6,041,260 A | 3/2000 | Stern et al. |
| 6,159,160 A | 12/2000 | Hsei et al. |
| 6,296,639 B1 | 10/2001 | Truckai et al. |
| 6,309,384 B1 | 10/2001 | Harrington et al. |
| 6,626,827 B1 | 9/2003 | Felix et al. |
| 6,663,626 B2 | 12/2003 | Truckai et al. |
| 6,736,811 B2 | 5/2004 | Panescu et al. |
| 6,813,520 B2 | 11/2004 | Truckai et al. |
| 6,872,183 B2 | 3/2005 | Sampson et al. |
| 7,073,504 B2 | 7/2006 | Callister et al. |
| 7,220,259 B2 | 5/2007 | Harrington et al. |
| 7,320,325 B2 | 1/2008 | Duchon et al. |
| 7,371,231 B2 | 5/2008 | Rioux et al. |
| 7,731,712 B2 | 6/2010 | Sampson et al. |
| 8,343,078 B2 * | 1/2013 | Toth ...................... A61B 5/035 600/560 |
| 9,289,257 B2 * | 3/2016 | Toth .................... A61B 5/1076 |
| 9,655,557 B2 | 5/2017 | Toth et al. |
| 2004/0215099 A1 | 10/2004 | Sampson et al. |
| 2005/0143728 A1 | 6/2005 | Sampson et al. |
| 2005/0240211 A1 | 10/2005 | Sporri et al. |
| 2007/0088344 A1 | 4/2007 | Schechter et al. |
| 2008/0097425 A1 | 4/2008 | Truckai |
| 2008/0167664 A1 | 7/2008 | Payne et al. |
| 2008/0178889 A1 | 7/2008 | Tal |
| 2008/0243054 A1 | 10/2008 | Mollstam et al. |
| 2009/0054892 A1 | 2/2009 | Rioux et al. |
| 2009/0149846 A1 | 6/2009 | Hoey et al. |
| 2010/0100091 A1 | 4/2010 | Truckai |
| 2010/0100094 A1 | 4/2010 | Truckai |
| 2010/0137857 A1 | 6/2010 | Shroff et al. |
| 2010/0198214 A1 | 8/2010 | Layton, Jr. et al. |
| 2011/0087109 A1 | 4/2011 | Swann |
| 2011/0112432 A1 | 5/2011 | Toth |

OTHER PUBLICATIONS

International search report and written opinion dated Sep. 28, 2012 for PCT/US2012/023548.
Notice of Allowance dated Jan. 18, 2017 for U.S. Appl. No. 13/361,089.
"Office action dated Mar. 6, 2014 for U.S. Appl. No. 13/361,089.".
"Office action dated Apr. 23, 2015 for U.S. Appl. No. 13/361,089.".
"Office action dated Aug. 13, 2015 for U.S. Appl. No. 13/361,089.".
Office action dated Aug. 22, 2016 for U.S. Appl. No. 13/361,089.
"Office action dated Sep. 25, 2014 for U.S. Appl. No. 13/361,089.".
Third party observations dated Sep. 6, 2013 for EP Application No. 10830743.0.

* cited by examiner

METHODS AND SYSTEMS FOR EVALUATING THE INTEGRITY OF A UTERINE CAVITY

CROSS-REFERENCE TO RELATED APPLICATION

This application is a divisional of U.S. patent application Ser. No. 13/361,089, filed Jan. 30, 2012, which claims the benefit of provisional application No. 61/439,788, filed on Feb. 4, 2011, the full disclosure of which is incorporated herein by reference.

BACKGROUND

1. Field of the Invention

The present invention relates to electrosurgical methods and devices for global endometrial ablation in a treatment of menorrhagia. More particularly, the present invention relates to applying radiofrequency current to endometrial tissue by means of capacitively coupling the current through an expandable, thin-wall dielectric member enclosing an ionized gas.

A variety of devices have been d or proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. Nos. 6,736,811 and 5,925,038 show an inflatable conductive electrode.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention provides methods, systems and devices for evaluating the integrity of a uterine cavity. The uterine cavity may be perforated or otherwise damaged by the transcervical introduction of probes and instruments into the uterine cavity. If the uterine wall is perforated, it would be preferable to defer any ablation treatment until the uterine wall is healed. A method of the invention comprises introducing transcervically a probe into a patient's uterine cavity, providing a flow of a fluid (e.g., $CO_2$) through the probe into the uterine cavity and monitoring the rate of the flow to characterize the uterine cavity as perforated or non-perforated based on a change in the flow rate. If the flow rate drops by at least 10%, usually at least 20%, preferably at least 30%, more preferably at least 40%, and typically by at least 50%, this indicates that the uterine cavity is intact and not perforated. If the flow rate does not drop significantly, this indicates that a fluid flow is leaking through a perforation in the uterine cavity into the uterine cavity or escaping around an occlusion balloon that occludes the cervical canal.

Embodiments herein provide a method and system for characterizing a patient's uterus, comprising introducing a flow of a fluid into a uterine cavity of a patient, typically at an initial flow rate from 0.05 standard liters per minute (slpm) to 0.2 slpm; and monitoring the flow to characterize the uterine cavity as at least one of perforated or non-perforated based on a change in a rate of the flow. Introducing may be, for example, transcervically introducing a probe into the uterine cavity, and introducing the flow through the probe, and the flow will typically be at a low pressure in the range from 0.025 psi to 1 psi.

Monitoring may include providing a signal, responsive to the rate of flow, that characterizes the uterine cavity as at least one of perforated or non-perforated. As an example, monitoring may include generating a signal responsive to the rate of flow not dropping below a predetermined level, the signal characterizing the uterine cavity as perforated. In embodiments, the predetermined level is typically in a range from 0.01 slpm to 0.05 slpm.

In embodiments, monitoring comprises generating a signal responsive to the rate of flow dropping below a predetermined level, the signal characterizing the uterine cavity as non-perforated. The predetermined level may be, for example, 0.05 slpm to 0.1 slpm.

In further embodiments, monitoring comprises monitoring a rate of flow after a predetermined first interval after initiation of the flow. The first interval may be, as examples, at least 5 seconds, at least 15 seconds, typically being in the range from 5 seconds to 30 seconds.

Monitoring may additionally include monitoring a rate of flow over a second predetermined interval after the first interval. The second interval may be a least 1 second, at least 5 seconds, or at least 10 seconds, as examples.

In additional embodiments, monitoring includes providing a signal, responsive to the rate of flow, that characterizes the uterine cavity as at least one of perforated or non-perforated, and wherein the signal is at least one of visual, aural and tactile.

In embodiments, prior to introducing the flow, a member is positioned within the cervical canal that substantially prevents a flow of the fluid out of the uterine cavity. Introducing may include transcervically introducing a probe into the uterine cavity, and introducing the flow through the probe, with the member positioned about an exterior of the probe. The member may be expanded in the cervical canal.

In embodiments, the fluid is a gas or a liquid.

In additional embodiments, introducing includes transcervically introducing a probe into the uterine cavity, and introducing the flow through the probe. The probe has a working end with an energy-delivery surface for ablating uterine cavity tissue. Responsive to the uterine cavity being characterized as perforated, energy delivery surface is disabled. Alternatively or additionally, responsive to the uterine cavity being characterized as non perforated, activation of the energy delivery surface may be enabled or even caused to happen automatically.

In embodiments, a method of endometrial ablation is provided, the method including introducing an ablation probe into a uterine cavity of a patient; flowing a fluid from a fluid source through the probe into the uterine cavity; monitoring the rate of the flow of the fluid into the uterine cavity to characterize the cavity as at least one of perforated or non-perforated based on a change in the flow rate; and responsive the to the uterine cavity being characterized as non perforated, activating the ablation probe to ablate an interior of the uterine cavity.

For a fuller understanding of the nature and advantages of the present invention, reference should be made to the ensuing detailed description and accompanying drawings.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

In general, an electrosurgical ablation system is described herein that comprises an elongated introducer member for accessing a patient's uterine cavity with a working end that deploys an expandable thin-wall dielectric structure containing an electrically non-conductive gas as a dielectric. In one embodiment, an interior chamber of the thin-wall dielectric structure contains a circulating neutral gas such as argon. An RF power source provides current that is coupled to the neutral gas flow by a first polarity electrode disposed within the interior chamber and a second polarity electrode at an exterior of the working end. The gas flow, which is converted to a conductive plasma by an electrode arrangement, functions as a switching mechanism that permits current flow to engaged endometrial tissue only when the voltage across the combination of the gas, the thin-wall dielectric structure and the engaged tissue reaches a threshold that causes capacitive coupling across the thin-wall dielectric material. By capacitively coupling current to tissue in this manner, the system provides a substantially uniform tissue effect within all tissue in contact with the expanded dielectric structure. Further, the invention allows the neutral gas to be created contemporaneously with the capacitive coupling of current to tissue.

In general, this disclosure may use the terms "plasma", "conductive gas" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Figure 1:
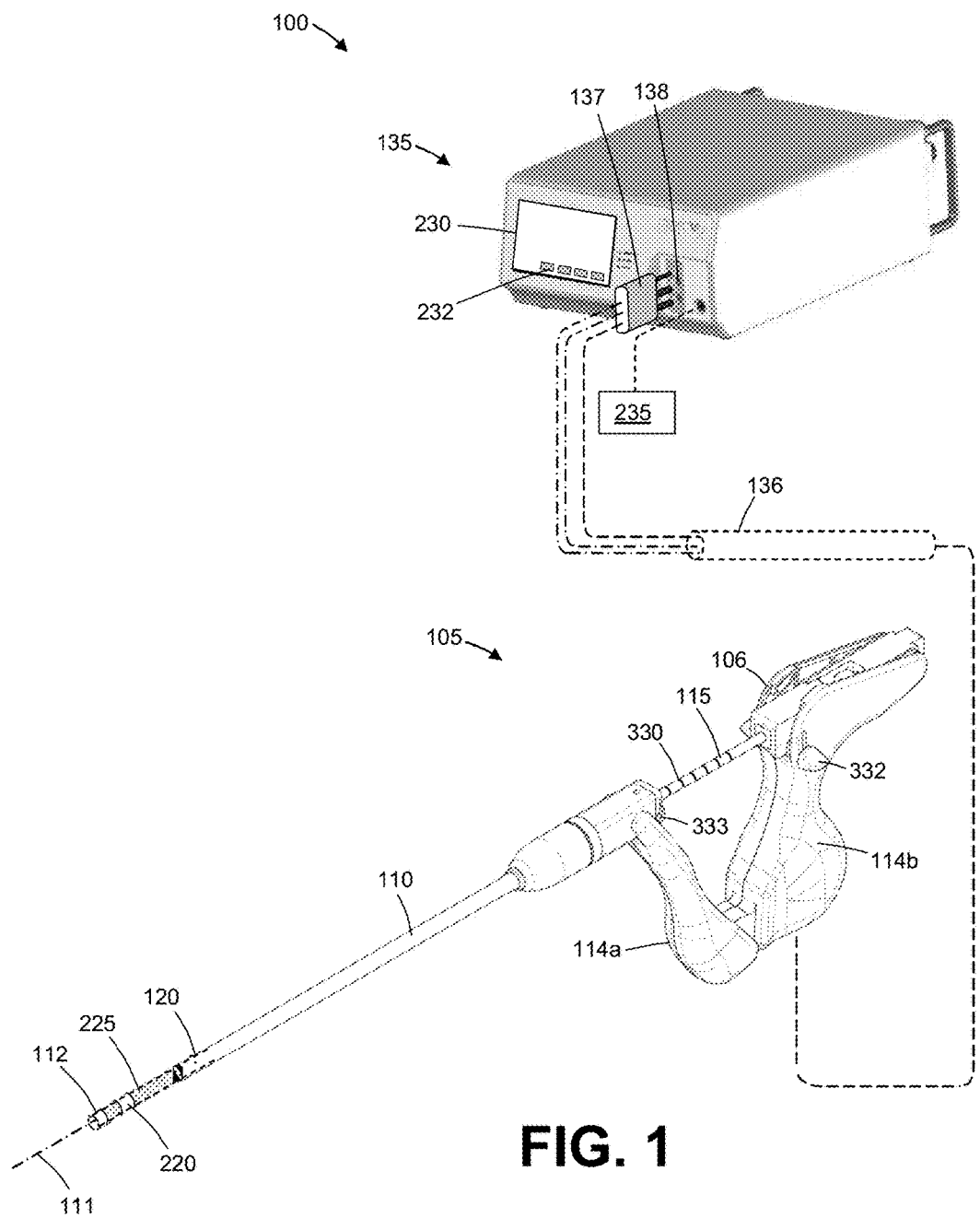
FIG. 1 is a perspective view of an ablation system corresponding to the invention, including a hand-held electrosurgical device for endometrial ablation, RF power source, gas source and controller.
Figure 2:
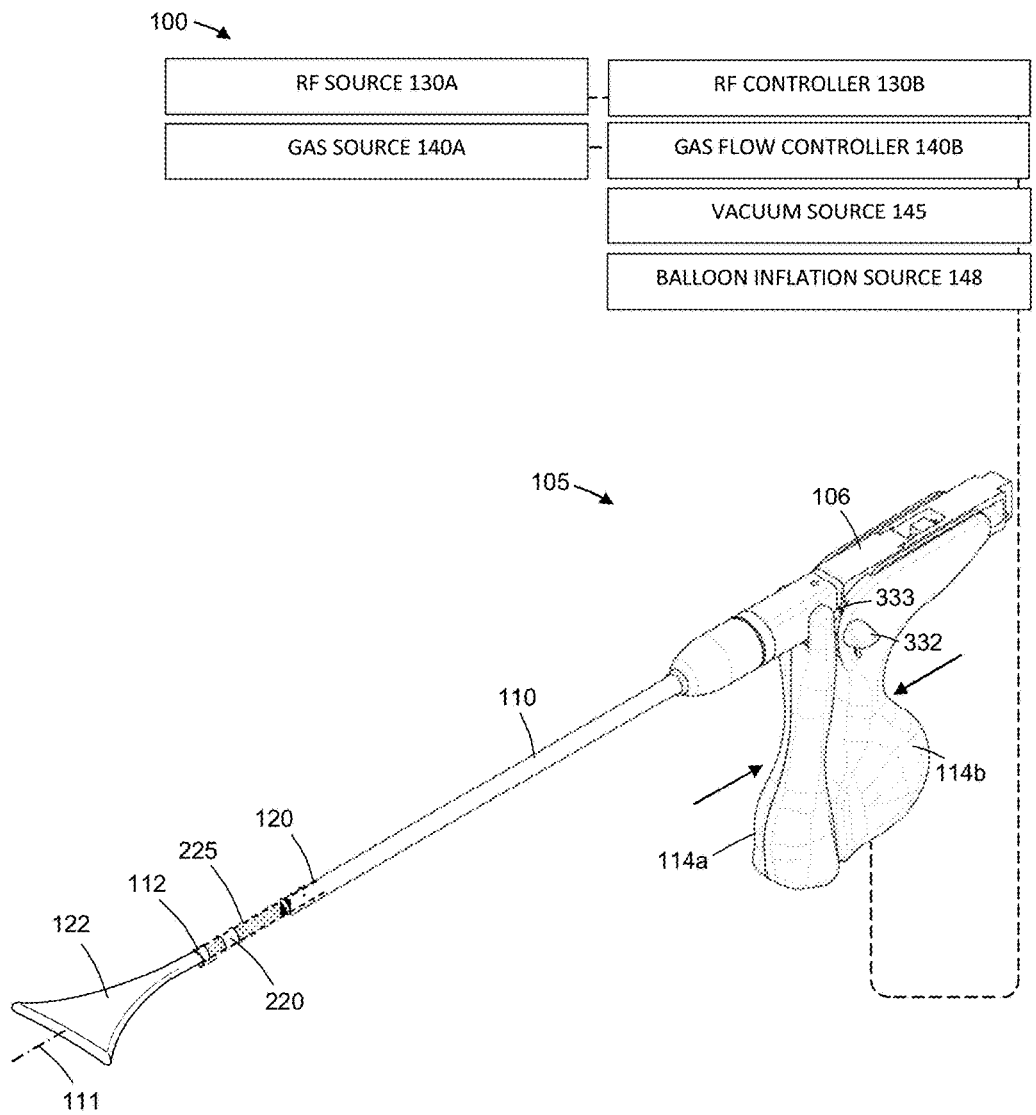
FIG. 2 is a view of the hand-held electrosurgical device of FIG. 1 with a deployed, expanded thin-wall dielectric structure.

FIG. 1 depicts one embodiment of an electrosurgical ablation system 100 configured for endometrial ablation. The system 100 includes a hand-held apparatus 105 with a proximal handle 106 shaped for grasping with a human hand that is coupled to an elongated introducer sleeve 110 having axis 111 that extends to a distal end 112. The introducer sleeve 110 can be fabricated of a thin-wall plastic, composite, ceramic or metal in a round or oval cross-section having a diameter or major axis ranging from about 4 mm to 8 mm in at least a distal portion of the sleeve that accesses the uterine cavity. The handle 106 is fabricated of an electrically insulative material such as a molded plastic with a pistol-grip having first and second portions, 114a and 114b, that can be squeezed toward one another to translate an elongated translatable sleeve 115 which is housed in a bore 120 in the elongated introducer sleeve 110. By actuating the first and second handle portions, 114a and 114b, a working end 122 can be deployed from a first retracted position (FIG. 1) in the distal portion of bore 120 in introducer sleeve 110 to an extended position as shown in FIG. 2. In FIG. 2, it can be seen that the first and second handle portions, 114a and 114b, are in a second actuated position with the working end 122 deployed from the bore 120 in introducer sleeve 110.

Figure 3:
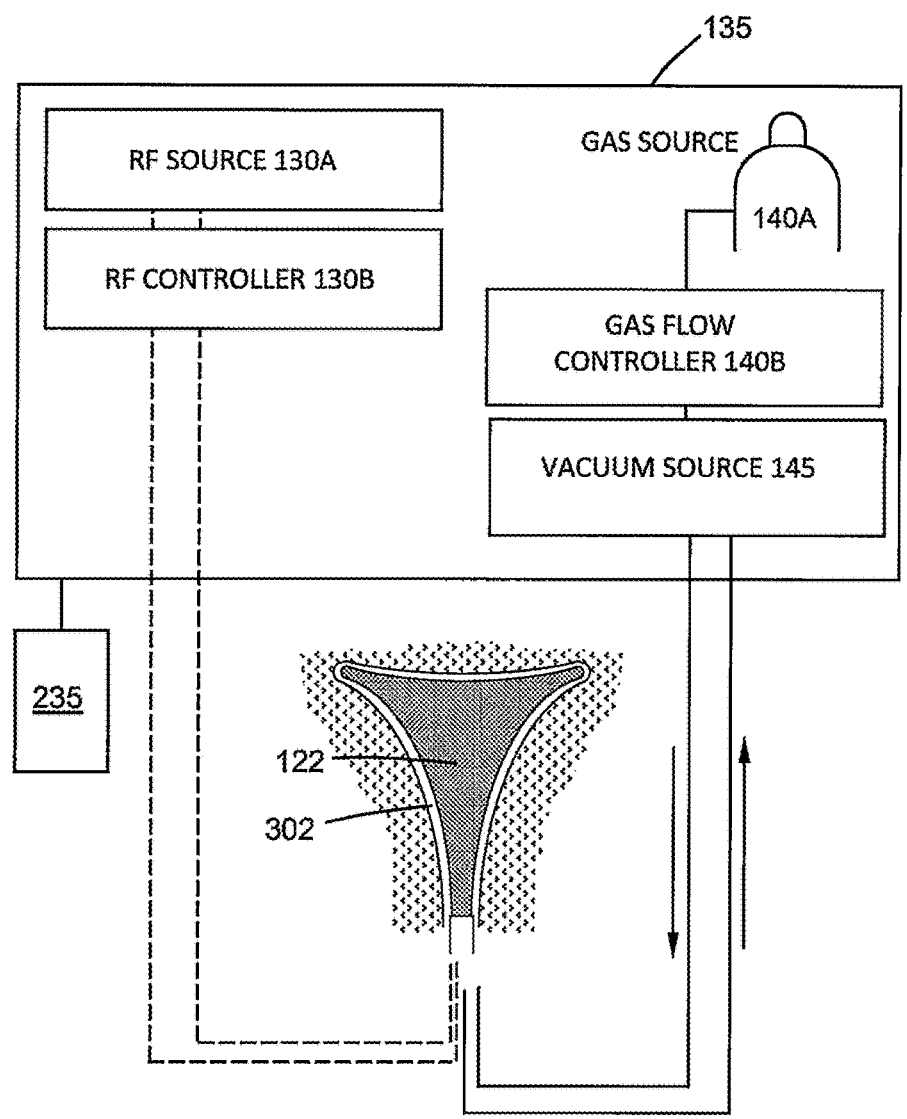
FIG. 3 is a block diagram of components of one electrosurgical system corresponding to the invention.

FIGS. 2 and 3 shows that ablation system 100 includes an RF energy source 130A and RF controller 130B in a control unit 135. The RF energy source 130A is connected to the hand-held device 105 by a flexible conduit 136 with a plug-in connector 137 configured with a gas inflow channel, a gas outflow channel, and first and second electrical leads for connecting to receiving connector 138 in the control unit 135. The control unit 135, as will be described further below in FIGS. 3 and 4, further comprises a neutral gas inflow source 140A, gas flow controller 140B and optional vacuum or negative pressure source 145 to provide controlled gas inflows and gas outflows to and from the working end 122. The control unit 135 further includes a balloon inflation source 148 for inflating an expandable sealing balloon 225 carried on introducer sleeve 110 as described further below.

Referring to FIG. 2, the working end 122 includes a flexible, thin-wall member or structure 150 of a dielectric material that when expanded has a triangular shape configured for contacting the patient's endometrial lining that is targeted for ablation. In one embodiment as shown in FIGS. 2, 5 and 6, the dielectric structure 150 comprises a thin-wall material such as silicone with a fluid-tight interior chamber 152.

In an embodiment, an expandable-collapsible frame assembly 155 is disposed in the interior chamber. Alternatively, the dielectric structure may be expanded by a neutral gas without a frame, but using a frame offers a number of advantages. First, the uterine cavity is flattened with the opposing walls in contact with one another. Expanding a balloon-type member may cause undesirable pain or spasms. For this reason, a flat structure that is expanded by a frame is better suited for deployment in the uterine cavity. Second, in embodiments herein, the neutral gas is converted to a conductive plasma at a very low pressure controlled by gas inflows and gas outflows—so that any pressurization of a balloon-type member with the neutral gas may exceed a desired pressure range and would require complex controls of gas inflows and gas outflows. Third, as described below, the frame provides an electrode for contact with the neutral gas in the interior chamber 152 of the dielectric structure 150, and the frame 155 extends into all regions of the interior chamber to insure electrode exposure to all regions of the neutral gas and plasma. The frame 155 can be constructed of any flexible material with at least portions of the frame functioning as spring elements to move the thin-wall structure 150 from a collapsed configuration (FIG. 1) to an expanded, deployed configuration (FIG. 2) in a patient's uterine cavity. In one embodiment, the frame 155 comprises stainless steel elements 158a, 158b and 160a and 160b that function akin to leaf springs. The frame can be a stainless steel such as 316 SS, 17A SS, 420 SS, 440 SS or the frame can be a NiTi material. The frame preferably extends along a single plane, yet remains thin transverse to the plane, so that the frame may expand into the uterine cavity. The frame elements can have a thickness ranging from about 0.005" to 0.025". As can be seen in FIGS. 5 and 6, the proximal ends 162a and 162b of spring elements 158a, 158b are fixed (e.g., by welds 164) to the distal end 165 of sleeve member 115. The proximal ends 166a and 166b of spring elements 160a, 160b are welded to distal portion 168 of a secondary translatable sleeve 170 that can be extended from bore 175 in translatable sleeve 115. The secondary translatable sleeve 170 is dimensioned for a loose fit in bore 175 to allow gas flows within bore 175. FIGS. 5 and 6 further illustrate the distal ends 176a and 176b of spring elements 158a, 158b are welded to distal ends 178a and 178b of spring elements 160a and 160b to thus provide a frame 155 that can be moved from a linear shape (see FIG. 1) to an expanded triangular shape (FIGS. 5 and 6).

As will be described further below, the bore 175 in sleeve 115 and bore 180 in secondary translatable sleeve 170 function as gas outflow and gas inflow lumens, respectively. It should be appreciated that the gas inflow lumen can comprise any single lumen or plurality of lumens in either sleeve 115 or sleeve 170 or another sleeve, or other parts of the frame 155 or the at least one gas flow lumen can be formed into a wall of dielectric structure 150. In FIGS. 5, 6 and 7 it can be seen that gas inflows are provided through bore 180 in sleeve 170, and gas outflows are provided in bore 175 of sleeve 115. However, the inflows and outflows can be also be reversed between bores 175 and 180 of the various sleeves. FIGS. 5 and 6 further show that a rounded bumper element 185 is provided at the distal end of sleeve 170 to insure that no sharp edges of the distal end of sleeve 170 can contact the inside of the thin dielectric wall 150. In one embodiment, the bumper element 185 is silicone, but it could also comprise a rounded metal element. FIGS. 5 and 6 also show that a plurality of gas inflow ports 188 can be provided along a length of in sleeve 170 in chamber 152, as well as a port 190 in the distal end of sleeve 170 and bumper element 185. The sectional view of FIG. 7 also shows the gas flow passageways within the interior of introducer sleeve 110.

Figure 5:
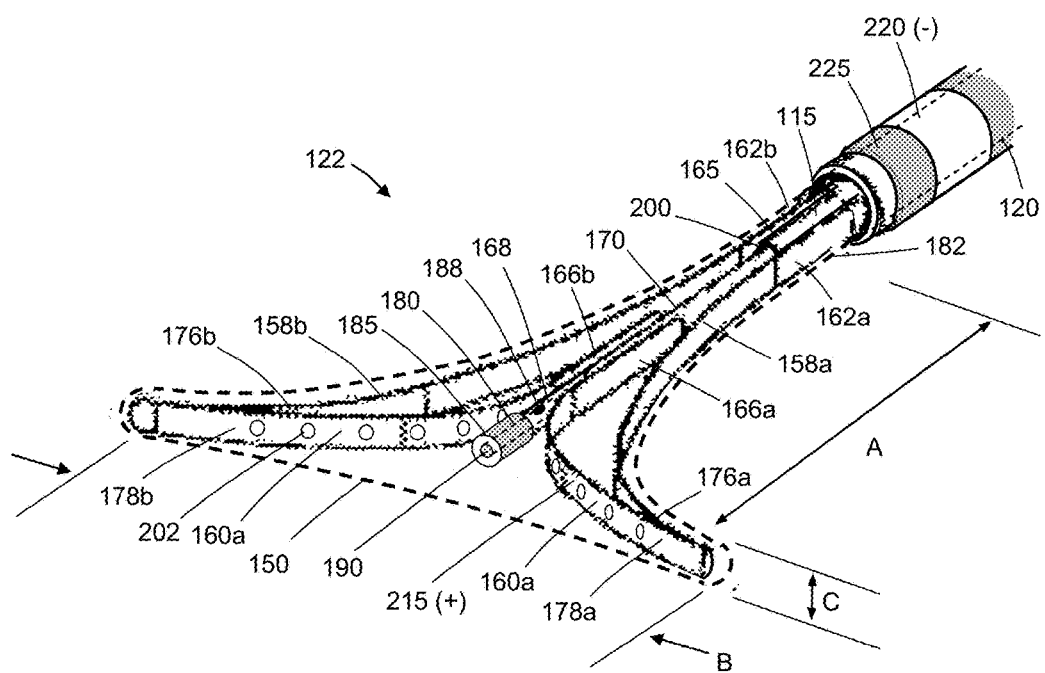
FIG. 5 is an enlarged perspective view of the expanded thin-wall dielectric structure, showing an expandable-collapsible frame with the thin dielectric wall in phantom view.
Figure 6:
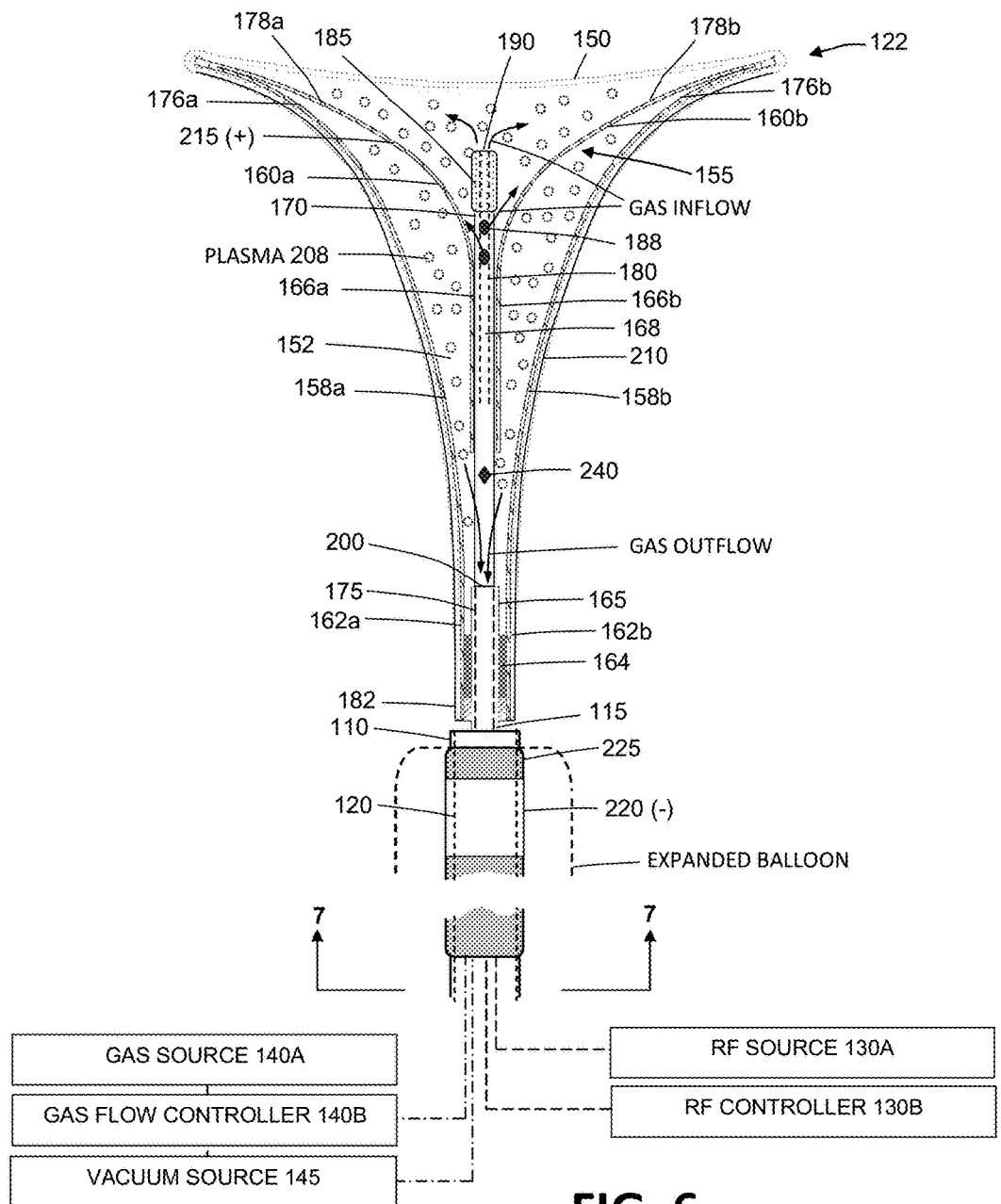
FIG. 6 is a partial sectional view of the expanded thin-wall dielectric structure of FIG. 5 showing (i) translatable members of the expandable-collapsible frame a that move the structure between collapsed and (ii) gas inflow and outflow lumens.
Figure 7:
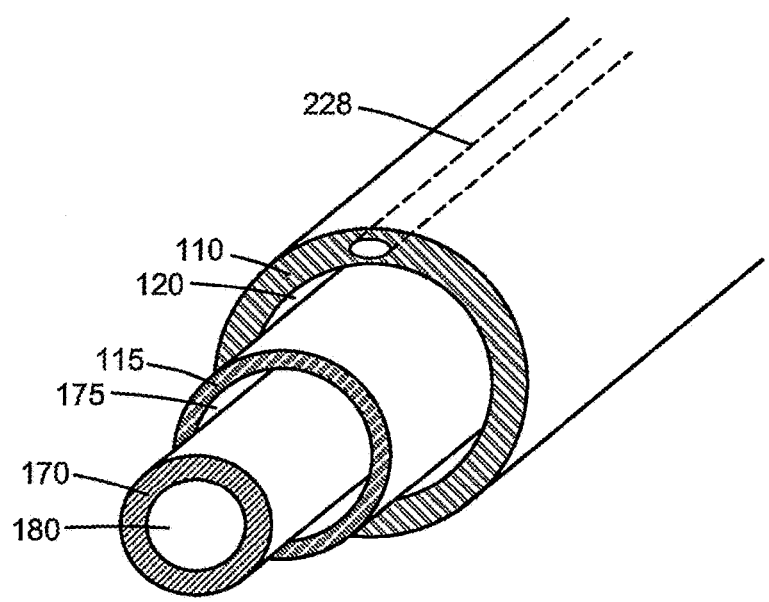
FIG. 7 is a sectional view of an introducer sleeve showing various lumens of the introducer sleeve taken along line 7-7 of FIG. 6.

It can be understood from FIGS. 1, 2, 5 and 6 that actuation of first and second handle portions, 114*a* and 114*b*, (i) initially causes movement of the assembly of sleeves 115 and 170 relative to bore 120 of introducer sleeve 110, and (ii) secondarily causes extension of sleeve 170 from bore 175 in sleeve 115 to expand the frame 155 into the triangular shape of FIG. 5. The dimensions of the triangular shape are suited for a patient uterine cavity, and for example can have an axial length A ranging from 4 to 10 cm and a maximum width B at the distal end ranging from about 2 to 5 cm. In one embodiment, the thickness C of the thin-wall structure 150 can be from 1 to 4 mm as determined by the dimensions of spring elements 158*a*, 158*b*, 160*a* and 160*b* of frame assembly 155. It should be appreciated that the frame assembly 155 can comprise round wire elements, flat spring elements, of any suitable metal or polymer that can provide opening forces to move thin-wall structure 150 from a collapsed configuration to an expanded configuration within the patient uterus. Alternatively, some elements of the frame 155 can be spring elements and some elements can be flexible without inherent spring characteristics.

As will be described below, the working end embodiment of FIGS. 2, 5 and 6 has a thin-wall structure 150 that is formed of a dielectric material such as silicone that permits capacitive coupling of current to engaged tissue while the frame assembly 155 provides structural support to position the thin-wall structure 150 against tissue. Further, gas inflows into the interior chamber 152 of the thin-wall structure can assist in supporting the dielectric wall so as to contact endometrial tissue. The dielectric thin-wall structure 150 can be free from fixation to the frame assembly 155, or can be bonded to an outward-facing portion or portions of frame elements 158*a* and 158*b*. The proximal end 182 of thin-wall structure 150 is bonded to the exterior of the distal end of sleeve 115 to thus provide a sealed, fluid-tight interior chamber 152 (FIG. 5).

In one embodiment, the gas inflow source 140A comprises one or more compressed gas cartridges that communicate with flexible conduit 136 through plug-in connector 137 and receiving connector 138 in the control unit 135 (FIGS. 1-2). As can be seen in FIGS. 5-6, the gas inflows from source 140A flow through bore 180 in sleeve 170 to open terminations 188 and 190 therein to flow into interior chamber 152. A vacuum source 145 is connected through conduit 136 and connector 137 to allow circulation of gas flow through the interior chamber 152 of the thin-wall dielectric structure 150. In FIGS. 5 and 6, it can be seen that gas outflows communicate with vacuum source 145 through open end 200 of bore 175 in sleeve 115. Referring to FIG. 5, it can be seen that frame elements 158*a* and 158*b* are configured with a plurality of apertures 202 to allow for gas flows through all interior portions of the frame elements, and thus gas inflows from open terminations 188, 190 in bore 180 are free to circulated through interior chamber 152 to return to an outflow path through open end 200 of bore 175 of sleeve 115. As will be described below (see FIGS. 3-4), the gas inflow source 140A is connected to a gas flow or circulation controller 140B which controls a pressure regulator 205 and also controls vacuum source 145 which is adapted for assisting in circulation of the gas. It should be appreciated that the frame elements can be configured with apertures, notched edges or any other configurations that allow for effective circulation of a gas through interior chamber 152 of the thin-wall structure 150 between the inflow and outflow passageways.

Now turning to the electrosurgical aspects of the invention, FIGS. 5 and 6 illustrate opposing polarity electrodes of the system 100 that are configured to convert a flow of neutral gas in chamber 152 into a plasma 208 (FIG. 6) and to allow capacitive coupling of current through a wall 210 of the thin-wall dielectric structure 150 to endometrial tissue in contact with the wall 210. The electrosurgical methods of capacitively coupling RF current across a plasma 208 and dielectric wall 210 are described in U.S. patent application Ser. No. 12/541,043; filed Aug. 13, 2009 and U.S. application Ser. No. 12/541,050 , referenced above. In FIGS. 5 and 6, the first polarity electrode 215 is within interior chamber 152 to contact the neutral gas flow and comprises the frame assembly 155 that is fabricated of an electrically conductive stainless steel. In another embodiment, the first polarity electrode can be any element disposed within the interior chamber 152, or extendable into interior chamber 152. The first polarity electrode 215 is electrically coupled to sleeves 115 and 170 which extends through the introducer sleeve 110 to handle 106 and conduit 136 and is connected to a first pole of the RF source energy source 130A and controller 130B. A second polarity electrode 220 is external of the internal chamber 152 and in one embodiment the electrode is spaced apart from wall 210 of the thin-wall dielectric structure 150. In one embodiment as depicted in FIGS. 5 and 6, the second polarity electrode 220 comprises a surface element of an expandable balloon member 225 carried by introducer sleeve 110. The second polarity electrode 220 is coupled by a lead (not shown) that extends through the introducer sleeve 110 and conduit 136 to a second pole of the RF source 130A. It should be appreciated that second polarity electrode 220 can be positioned on sleeve 110 or can be attached to surface portions of the expandable thin-wall dielectric structure 150, as will be described below, to provide suitable contact with body tissue to allow the electrosurgical ablation of the method of the invention. The second polarity electrode 220 can comprise a thin conductive metallic film, thin metal wires, a conductive flexible polymer or a polymeric positive temperature coefficient material. In one embodiment depicted in FIGS. 5 and 6, the expandable member 225 comprises a thin-wall compliant balloon having a length of about 1 cm to 6 cm that can be expanded to seal the cervical canal. The balloon 225 can be inflated with a gas or liquid by any inflation source 148, and can comprise a syringe mechanism controlled manually or by control unit 135. The balloon inflation source 148 is in fluid communication with an inflation lumen 228 in introducer sleeve 110 that extends to an inflation chamber of balloon 225 (see FIG. 7).

Referring back to FIG. 1, the control unit 135 can include a display 230 and touch screen or other controls 232 for setting and controlling operational parameters such as treatment time intervals, treatment algorithms, gas flows, power levels and the like. Suitable gases for use in the system include argon, other noble gases and mixtures thereof. In one embodiment, a footswitch 235 is coupled to the control unit 135 for actuating the system.

Figure 4:
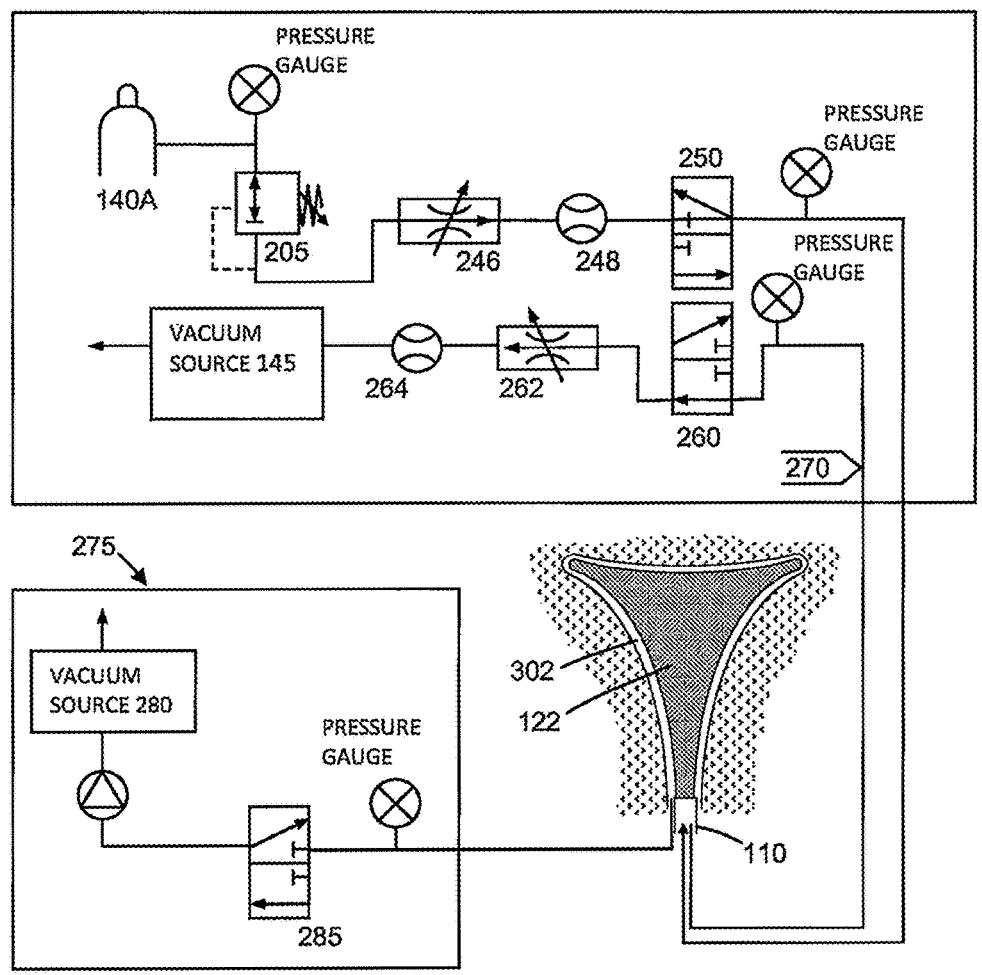
FIG. 4 s a block diagram of the gas flow components of the electrosurgical system of FIG. 1.

The box diagrams of FIGS. 3 and 4 schematically depict the system 100, subsystems and components that are configured for an endometrial ablation system. In the box diagram of FIG. 3, it can be seen that RF energy source 130A and circuitry is controlled by a controller 130B. The system can include feedback control systems that include signals relating to operating parameters of the plasma in interior chamber 152 of the dielectric structure 150. For example, feedback signals can be provided from at least one temperature sensor 240 in the interior chamber 152 of the dielectric structure 150, from a pressure sensor within, or in communication, with interior chamber 152, and/or from a gas flow rate sensor in an inflow or outflow channel of the system. FIG. 4 is a schematic block diagram of the flow control components relating to the flow of gas media through the system 100 and hand-held device 105. It can be seen that a pressurized gas source 140A is linked to a downstream pressure regulator 205, an inflow proportional valve 246, flow meter 248 and normally closed solenoid valve 250. The valve 250 is actuated by the system operator which then allows a flow of a neutral gas from gas source 140A to circulate through flexible conduit 136 and the device 105. The gas outflow side of the system includes a normally open solenoid valve 260, outflow proportional valve 262 and flow meter 264 that communicate with vacuum pump or source 145. The gas can be exhausted into the environment or into a containment system. A temperature sensor 270 (e.g., thermocouple) is shown in FIG. 4 that is configured for monitoring the temperature of outflow gases. FIG. 4 further depicts an optional subsystem 275 which comprises a vacuum source 280 and solenoid valve 285 coupled to the controller 140B for suctioning steam from a uterine cavity 302 at an exterior of the dielectric structure 150 during a treatment interval. As can be understood from FIG. 4, the flow passageway from the uterine cavity 302 can be through bore 120 in sleeve 110 (see FIGS. 2, 6 and 7) or another lumen in a wall of sleeve 110 can be provided.

FIGS. 8A-8D schematically illustrate a method of the invention wherein (i) the thin-wall dielectric structure 150 is deployed within a patient uterus and (ii) RF current is applied to a contained neutral gas volume in the interior chamber 152 to contemporaneously create a plasma 208 in the chamber and capacitively couple current through the thin dielectric wall 210 to apply ablative energy to the endometrial lining to accomplish global endometrial ablation.

Figure 8A:
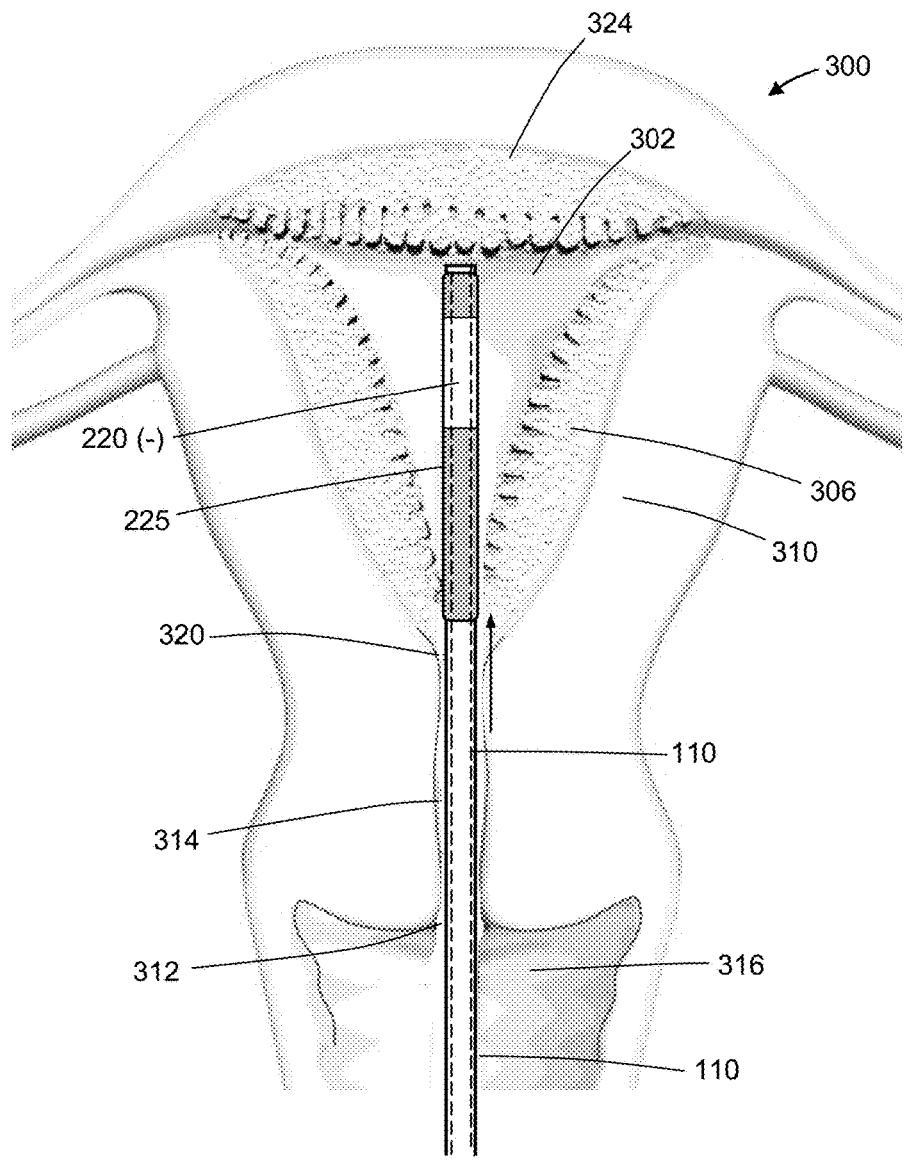
FIG. 8A is an enlarged schematic view of an aspect of a method of the invention illustrating the step introducing an introducer sleeve into a patient's uterus.

More in particular, FIG. 8A illustrates a patient uterus 300 with uterine cavity 302 surrounded by endometrium 306 and myometrium 310. The external cervical os 312 is the opening of the cervix 314 into the vagina 316. The internal os or opening 320 is a region of the cervical canal that opens to the uterine cavity 302. FIG. 8A depicts a first step of a method of the invention wherein the physician has introduced a distal portion of sleeve 110 into the uterine cavity 302. The physician gently can advance the sleeve 110 until its distal tip contacts the fundus 324 of the uterus. Prior to insertion of the device, the physician can optionally introduce a sounding instrument into the uterine cavity to determine uterine dimensions, for example from the internal os 320 to fundus 324.

Figure 8B:
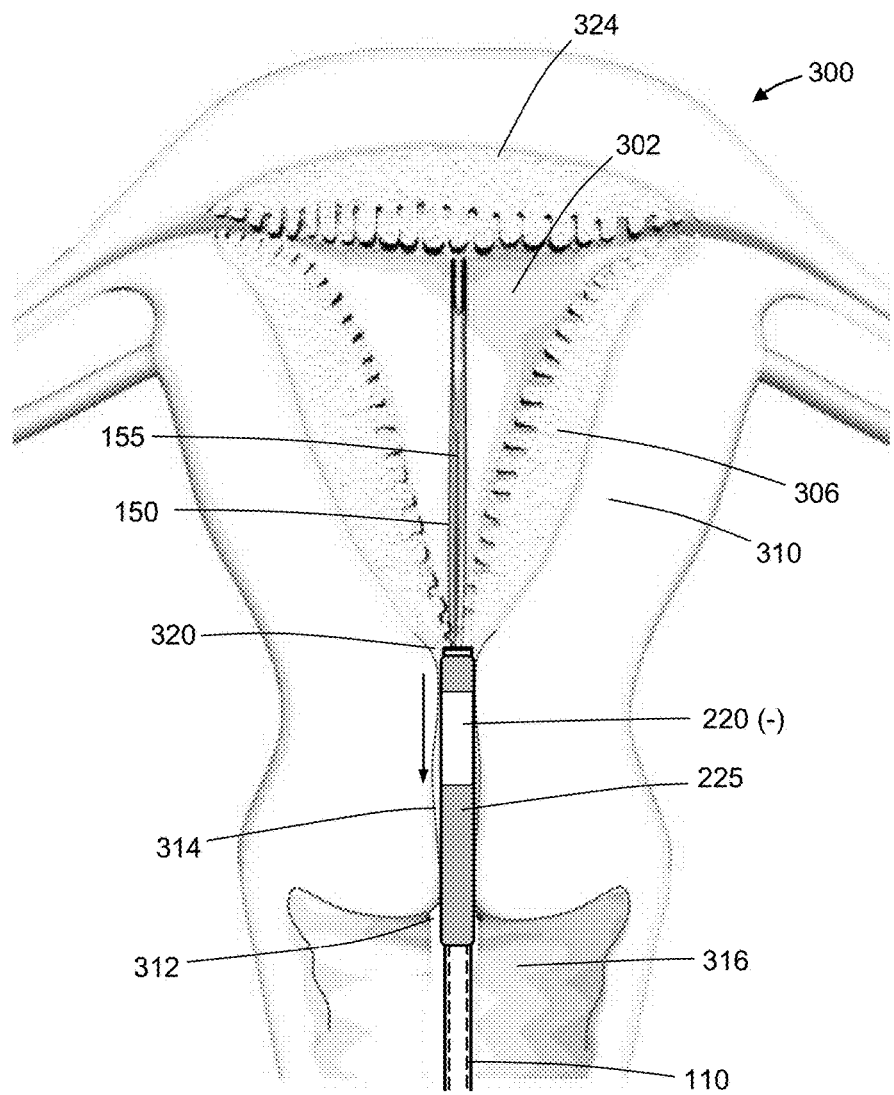
FIG. 8B is a schematic view of a subsequent step of retracting the introducer sleeve to expose a collapsed thin-wall dielectric structure and internal frame in the uterine cavity.

FIG. 8B illustrates a subsequent step of a method of the invention wherein the physician begins to actuate the first and second handle portions, 114a and 114b, and the introducer sleeve 110 retracts in the proximal direction to expose the collapsed frame 155 and thin-wall structure 150 within the uterine cavity 302. The sleeve 110 can be retracted to expose a selected axial length of thin-wall dielectric structure 150, which can be determined by markings 330 on sleeve 115 (see FIG. 1) which indicate the axial travel of sleeve 115 relative to sleeve 170 and thus directly related to the length of deployed thin-wall structure 150. FIG. 2 depicts the handle portions 114a and 114b fully approximated thus deploying the thin-wall structure to its maximum length.

Figure 8C:
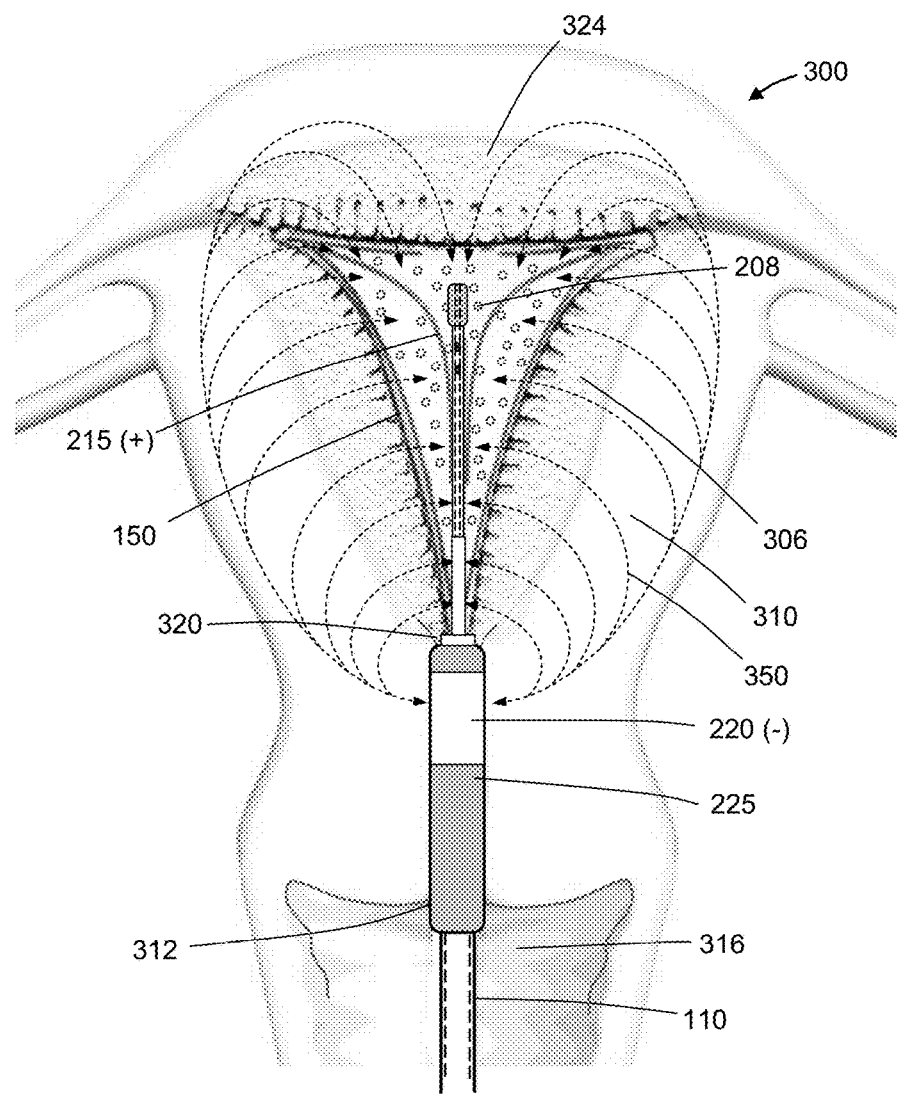
FIG. 8C is a schematic view of subsequent steps of the method, including, (i) actuating the internal frame to move the a collapsed thin-wall dielectric structure to an expanded configuration, (ii) inflating a cervical-sealing balloon carried on the introducer sleeve, and (iii) actuating gas flows and applying RF energy to contemporaneously ionize the gas in the interior chamber and cause capacitive coupling of current through the thin-wall dielectric structure to cause ohmic heating in the engaged tissue indicated by current flow paths.

FIG. 8C illustrates several subsequent steps of a method of the invention. FIG. 8C first depicts the physician continuing to actuate the first and second handle portions, 114a and 114b, which further actuates the frame 155 (see FIGS. 5-6) to expand the frame 155 and thin-wall structure 150 to a deployed triangular shape to contact the patient's endometrial lining 306. The physician can slightly rotate and move the expanding dielectric structure 150 back and forth as the structure is opened to insure it is opened to the desired extent. In performing this step, the physician can actuate handle portions, 114a and 114b, a selected degree which causes a select length of travel of sleeve 170 relative to sleeve 115 which in turn opens the frame 155 to a selected degree. The selected actuation of sleeve 170 relative to sleeve 115 also controls the length of dielectric structure deployed from sleeve 110 into the uterine cavity. Thus, the thin-wall structure 150 can be deployed in the uterine cavity with a selected length, and the spring force of the elements of frame 155 will open the structure 150 to a selected triangular shape to contact or engage the endometrium 306. In one embodiment, the expandable thin-wall structure 150 is urged toward and maintained in an open position by the spring force of elements of the frame 155. In the embodiment depicted in FIGS. 1 and 2, the handle 106 includes a locking mechanism with finger-actuated sliders 332 on either side of the handle that engage a grip-lock element against a notch in housing 333 coupled to introducer sleeve 110 (FIG. 2) to lock sleeves 115 and 170 relative to introducer sleeve 110 to maintain the thin-wall dielectric structure 150 in the selected open position.

FIG. 8C further illustrates the physician expanding the expandable balloon structure 225 from inflation source 148 to thus provide an elongated sealing member to seal the cervix 314 outward from the internal os 320. Following deployment of the thin-wall structure 150 and balloon 225 in the cervix 314, the system 100 is ready for the application of RF energy to ablate endometrial tissue 306. FIG. 8C next depicts the actuation of the system 100, for example, by actuating footswitch 235, which commences a flow of neutral gas from source 140A into the interior chamber 152 of the thin-wall dielectric structure 150. Contemporaneous with, or after a selected delay, the system's actuation delivers RF energy to the electrode arrangement which includes first polarity electrode 215 (+) of frame 155 and the second polarity electrode 220 (−) which is carried on the surface of expandable balloon member 225. The delivery of RF energy delivery will instantly convert the neutral gas in interior chamber 152 into conductive plasma 208 which in turn results in capacitive coupling of current through the dielectric wall 210 of the thin-wall structure 150 resulting in ohmic heating of the engaged tissue. FIG. 8C schematically illustrates the multiplicity of RF current paths 350 between the plasma 208 and the second polarity electrode 220 through the dielectric wall 210. By this method, it has been found that ablation depths of three mm to six mm or more can be accomplished very rapidly, for example in 60 seconds to 120 seconds dependent upon the selected voltage and other operating parameters. In operation, the voltage at which the neutral gas inflow, such as argon, becomes conductive (i.e., converted in part into a plasma) is dependent upon a number of factors controlled by the controllers 130B and 140B, including the pressure of the neutral gas, the volume of interior chamber 152, the flow rate of the gas through the chamber 152, the distance between electrode 210 and interior surfaces of the dielectric wall 210, the dielectric constant of the dielectric wall 210 and the selected voltage applied by the RF source 130, all of which can be optimized by experimentation. In one embodiment, the gas flow rate can be in the range of 5 ml/sec to 50 ml/sec. The dielectric wall 210 can comprise a silicone material having a thickness ranging from a 0.005" to 0.015 and having a relative permittivity in the range of 3 to 4. The gas can be argon supplied in a pressurized cartridge which is commercially available. Pressure in the interior chamber 152 of dielectric structure 150 can be maintained between 14 psia and 15 psia with zero or negative differential pressure between gas inflow source 140A and negative pressure or vacuum source 145. The controller is configured to maintain the pressure in interior chamber in a range that varies by less than 10% or less than 5% from a target pressure. The RF power source 130A can have a frequency of 450 to 550 KHz, and electrical power can be provided within the range of 600 Vrms to about 1200 Vrms and about 0.2 Amps to 0.4 Amps and an effective power of 40 W to 100 W. In one method, the control unit 135 can be programmed to delivery RF energy for a preselected time interval, for example, between 60 seconds and 120 seconds. One aspect of a treatment method corresponding to the invention consists of ablating endometrial tissue with RF energy to elevate endometrial tissue to a temperature greater than 45 degrees Celsius for a time interval sufficient to ablate tissue to a depth of at least 1 mm. Another aspect of the method of endometrial ablation of consists of applying radiofrequency energy to elevate endometrial tissue to a temperature greater than 45 degrees Celsius without damaging the myometrium.

Figure 8D:
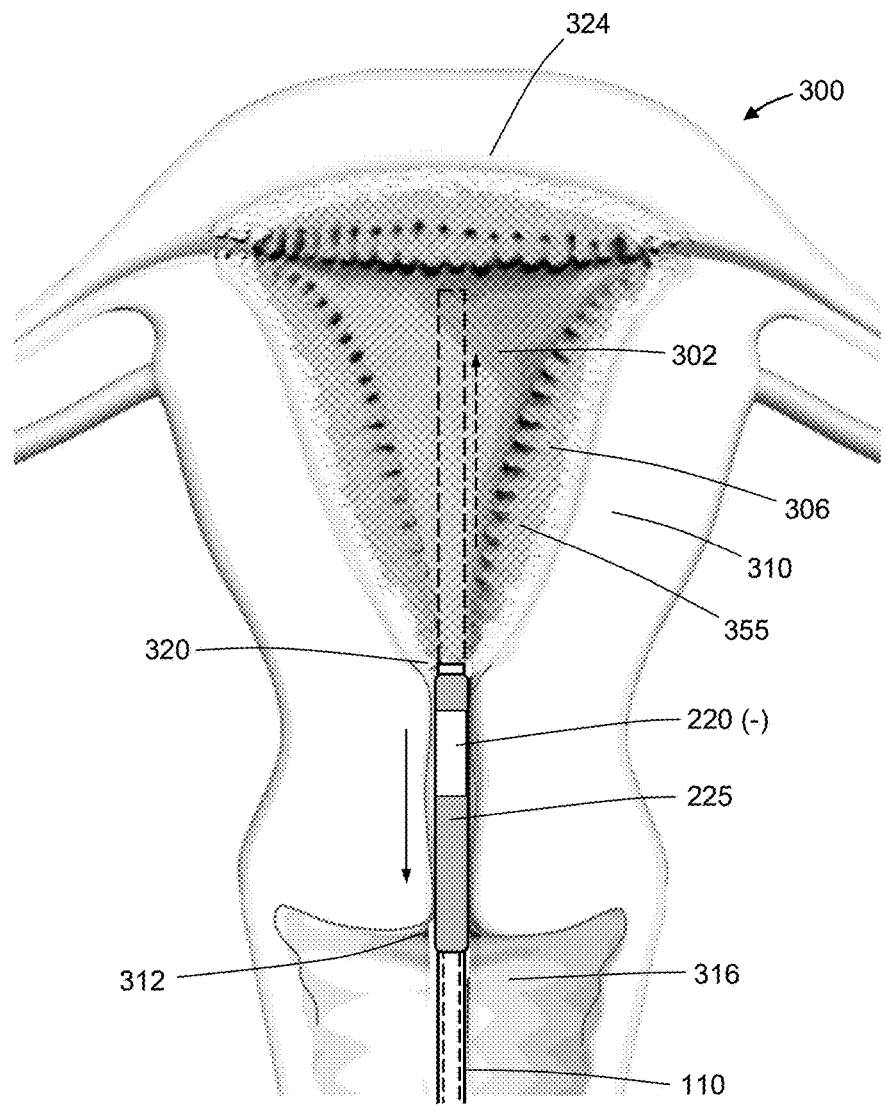
FIG. 8D is a schematic view of a subsequent steps of the method, including: (i) advancing the introducer sleeve over the thin-wall dielectric structure to collapse it into an interior bore shown in phantom view, and (ii) withdrawing the introducer sleeve and dielectric structure from the uterine cavity.

FIG. 8D illustrates a final step of the method wherein the physician deflates the expandable balloon member 225 and then extends sleeve 110 distally by actuating the handles 114a and 114b to collapse frame 155 and then retracting the assembly from the uterine cavity 302. Alternatively, the deployed working end 122 as shown in FIG. 8C can be withdrawn in the proximal direction from the uterine cavity wherein the frame 155 and thin-wall structure 150 will collapse as it is pulled through the cervix. FIG. 8D shows the completed ablation with the ablated endometrial tissue indicated at 360.

In another embodiment, the system can include an electrode arrangement in the handle 106 or within the gas inflow channel to pre-ionize the neutral gas flow before it reaches the interior chamber 152. For example, the gas inflow channel can be configured with axially or radially spaced apart opposing polarity electrodes configured to ionize the gas inflow. Such electrodes would be connected in separate circuitry to an RF source. The first and second electrodes 215 (+) and 220 (−) described above would operate as described above to provide the current that is capacitively coupled to tissue through the walls of the dielectric structure 150. In all other respects, the system and method would function as described above.

Figure 9:
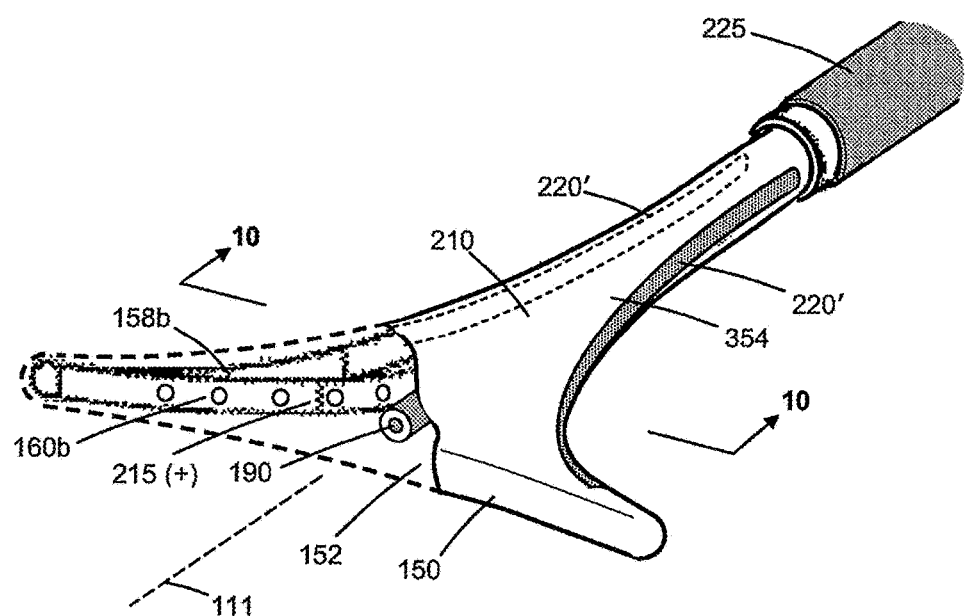
FIG. 9 is a cut-away perspective view of an alternative expanded thin-wall dielectric structure similar to that of FIGS. 5 and 6 show an alternative electrode configuration.
Figure 10:
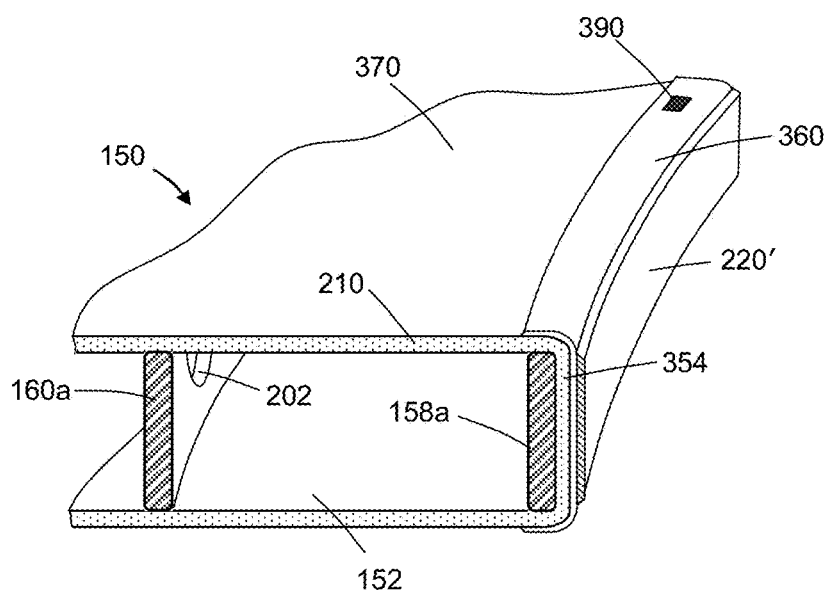
FIG. 10 is an enlarged cut-away view of a portion of the expanded thin-wall dielectric structure of FIG. 9 showing the electrode configuration.

Now turning to FIGS. 9 and 10, an alternate working end 122 with thin-wall dielectric structure 150 is shown. In this embodiment, the thin-wall dielectric structure 150 is similar to that of FIGS. 5 and 6 except that the second polarity electrode 220' that is exterior of the internal chamber 152 is disposed on a surface portion 370 of the thin-wall dielectric structure 150. In this embodiment, the second polarity electrode 220' comprises a thin-film conductive material, such as gold, that is bonded to the exterior of thin-wall material 210 along two lateral sides 354 of dielectric structure 150. It should be appreciated that the second polarity electrode can comprise one or more conductive elements disposed on the exterior of wall material 210, and can extend axially, or transversely to axis 111 and can be singular or multiple elements. In one embodiment shown in more detail in FIG. 10, the second polarity electrode 220' can be fixed on another lubricious layer 360, such as a polyimide film, for example KAPTON®. The polyimide tape extends about the lateral sides 354 of the dielectric structure 150 and provides protection to the wall 210 when it is advanced from or withdrawn into bore 120 in sleeve 110. In operation, the RF delivery method using the embodiment of FIGS. 9 and 10 is the same as described above, with RF current being capacitively coupled from the plasma 208 through the wall 210 and endometrial tissue to the second polarity electrode 220' to cause the ablation.

FIG. 9 further shows an optional temperature sensor 390, such as a thermocouple, carried at an exterior of the dielectric structure 150. In one method of use, the control unit 135 can acquire temperature feedback signals from at least one temperature sensor 390 to modulate or terminate RF energy delivery, or to modulate gas flows within the system. In a related method of the invention, the control unit 135 can acquire temperature feedback signals from temperature sensor 240 in interior chamber 152 (FIG. 6 to modulate or terminate RF energy delivery or to modulate gas flows within the system.

In another embodiment of the invention, FIGS. 11-14 depict systems and methods for evaluating the integrity of the uterine cavity which may be perforated or otherwise damaged by the transcervical introduction of probes and instruments into a uterine cavity. If the uterine wall is perforated, it would be preferable to defer any ablation treatment until the uterine wall is healed. A method of the invention comprises introducing transcervically a probe into a patient's uterine cavity, providing a flow of a fluid (e.g., CO2) through the probe into the uterine cavity and monitoring the rate of the flow to characterize the uterine cavity as perforated or non-perforated based on a change in the flow rate. If the flow rate drops to zero or close to zero, this indicates that the uterine cavity is intact and not perforated. If the flow rate does not drop to zero or close to zero, this indicates that a fluid flow is leaking through a perforation in the uterine cavity 302 into the uterine cavity or escaping around an occlusion balloon that occludes the cervical canal.

Figure 11:
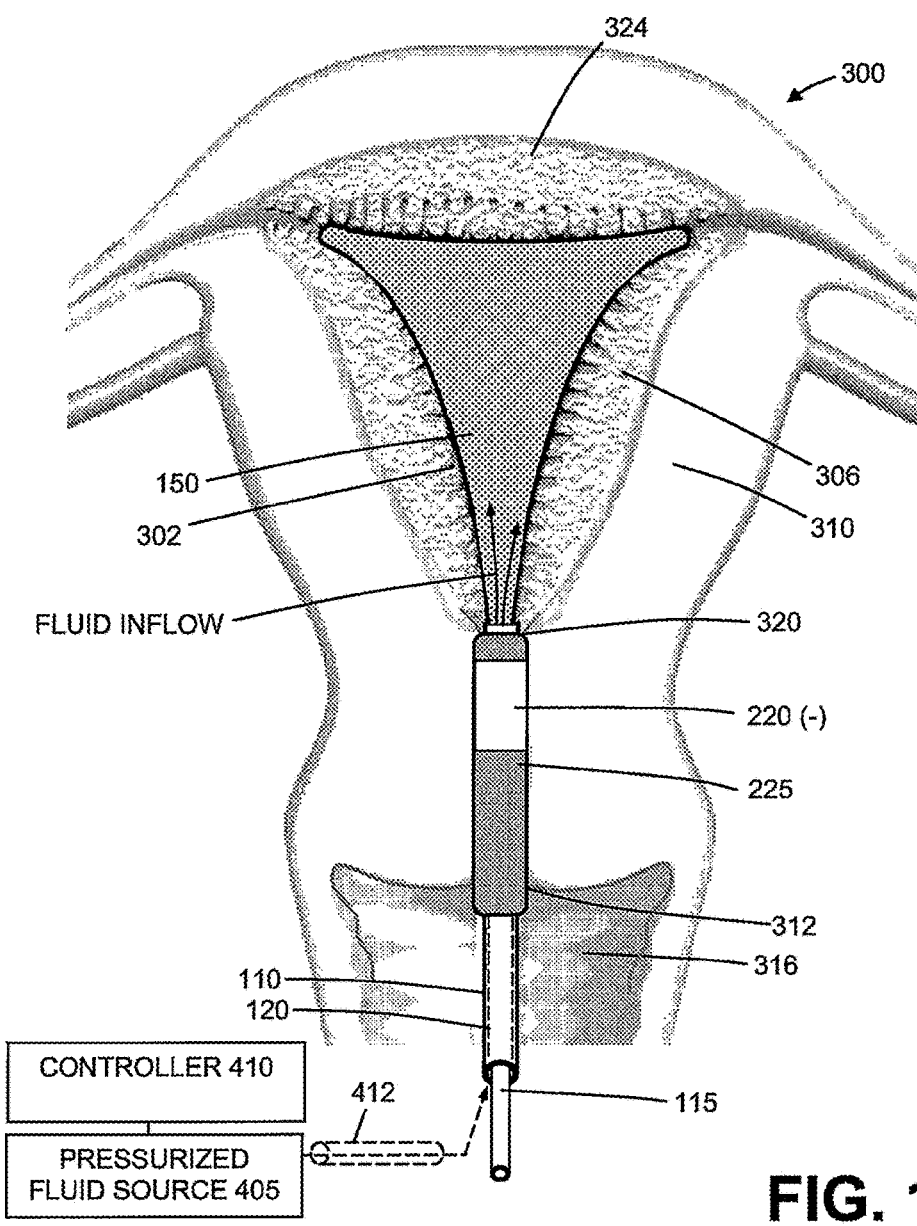
FIG. 11 is a schematic view of a patient uterus depicting a method corresponding to the invention including providing a flow of a fluid media into the uterine cavity and monitoring the flow rate to characterize the patient's uterine cavity as intact and non-perforated.
Figure 12:
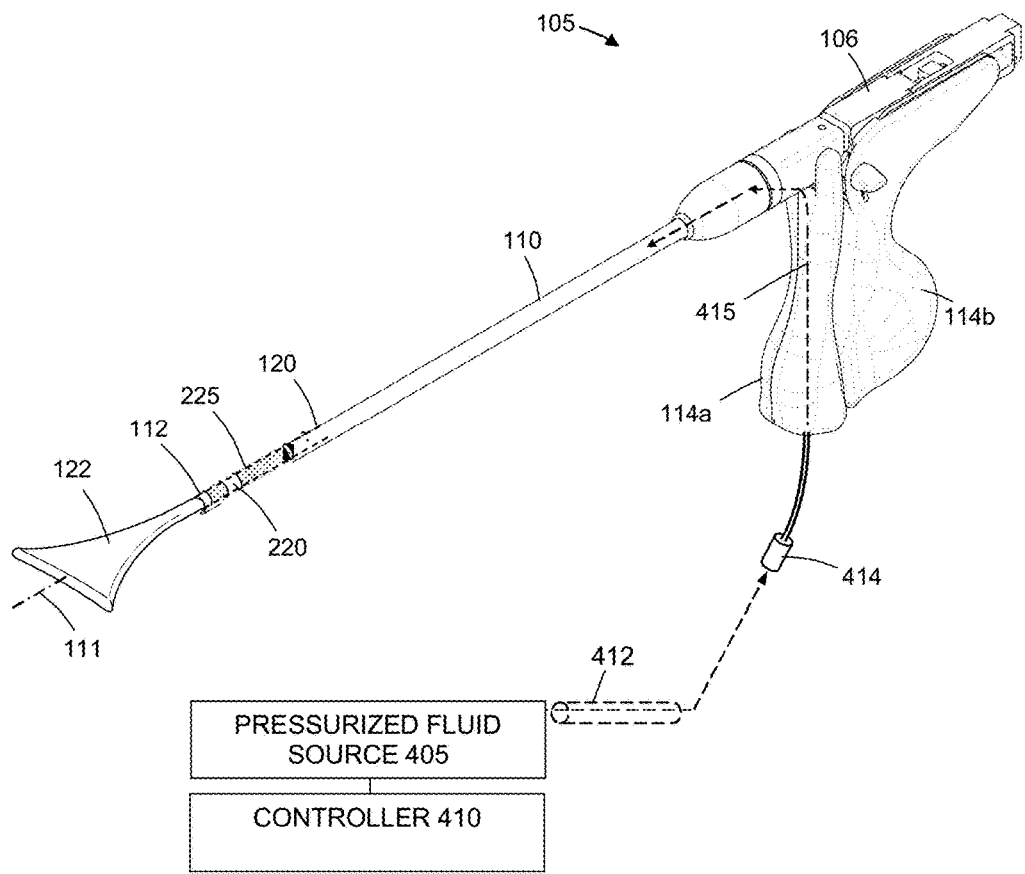
FIG. 12 is a perspective view of the ablation device of FIGS. 1-2 with a subsystem for checking the integrity of a uterine cavity.

In FIG. 11, it can be seen how a pressurized fluid source 405 and controller 410 for controlling and monitoring flows is in fluid communication with lumen 120 of introducer sleeve 110 (see FIG. 7). In one embodiment, the fluid source can be a pressurized cartridge containing CO2 or another biocompatible gas. In FIG. 12, it can be seen that fluid source 405 communicates with a flexible conduit 412 that is connected to a "pig-tail" tubing connector 414 extending outward from handle 106 of the hand-held probe. A tubing in the interior of handle component 114a provides a flow passageway 415 to the lumen 120 in the introducer sleeve. In another embodiment, the fluid source 405 and flexible conduit 408 can be integrated into conduit 136 of FIG. 1.

In FIG. 11, it can be seen that the flow of fluid is introduced into the uterine cavity 302 after the balloon 225 in the cervical canal has been inflated and after the working end and dielectric structure 150 has been expanded into its triangular shape to occupy the uterine cavity. Thus, the CO2 gas flows around the exterior surfaces of expanded dielectric structure 150 to fill the uterine cavity. Alternatively, the flow of CO2 can be provided after the balloon 225 in the cervical canal is inflated but before the dielectric structure 150 is expanded.

Figure 13:
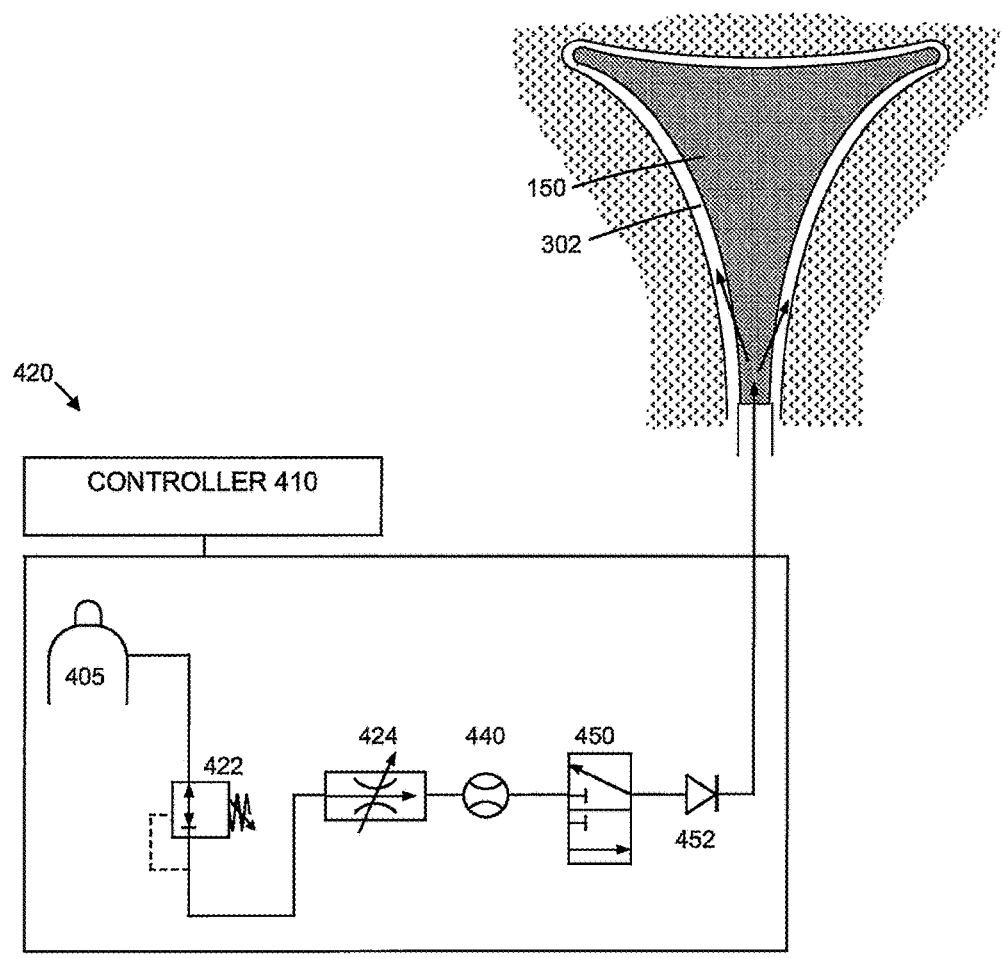
FIG. 13 represents a block diagram of a subsystem of the invention for providing and monitoring a fluid flow into the patient's uterine cavity.

FIG. 13 is a block diagram that schematically depicts the components of subsystem 420 that provides the flow of CO2 to and through the hand-held probe 105. It can be seen that pressurized fluid source 405 communicates with a downstream pressure regulator 422, a proportional valve 424, flow meter 440, normally closed solenoid valve 450 and one-way valve 452. The valve 450 upon actuation by the system operator allows a flow of CO2 gas from source 405 at a predetermined flow rate and pressure through the subsystem and into the uterine cavity 302.

In one embodiment of the method of operation, the physician actuates the system and electronically opens valve 450 which can provide a CO2 flow through the system. The controller 410 monitors the flow meter or sensor 440 over an interval that can range from 1 second to 60 seconds, or 5 second to 30 seconds to determine the change in the rate of flow and/or a change in the rate of flow. In an embodiment, the flow sensor comprises a Honeywell AWM5000 Series Mass Airflow Sensor, for example Model AWM5101, that measure flows in units of mass flow. In one embodiment, the initial flow rate is between 0.05 slpm (standard liters per minute) and 2.0 slpm, or between 0.1 slpm and 0.2 slpm. The controller 410 includes a microprocessor or programmable logic device that provides a feedback signal from the flow sensors indicating either (i) that the flow rate has dropped to zero or close to zero to thus characterize the uterine cavity as non-perforated, or (ii) that the flow rate has not dropped to a predetermined threshold level within a predetermined time interval to thus characterize the uterine cavity as perforated or that there is a failure in occlusion balloon 225 or its deployment so that the cervical canal is not occluded. In one embodiment, the threshold level is 0.05 slpm for characterizing the uterine cavity as non-perforated. In this embodiment, the controller provides a signal indicating a non-perforated uterine cavity if the flow drops below 0.05 slpm between the fifth second of the flow and the flow time-out, which can be, for example, 30 seconds.

Figure 14:
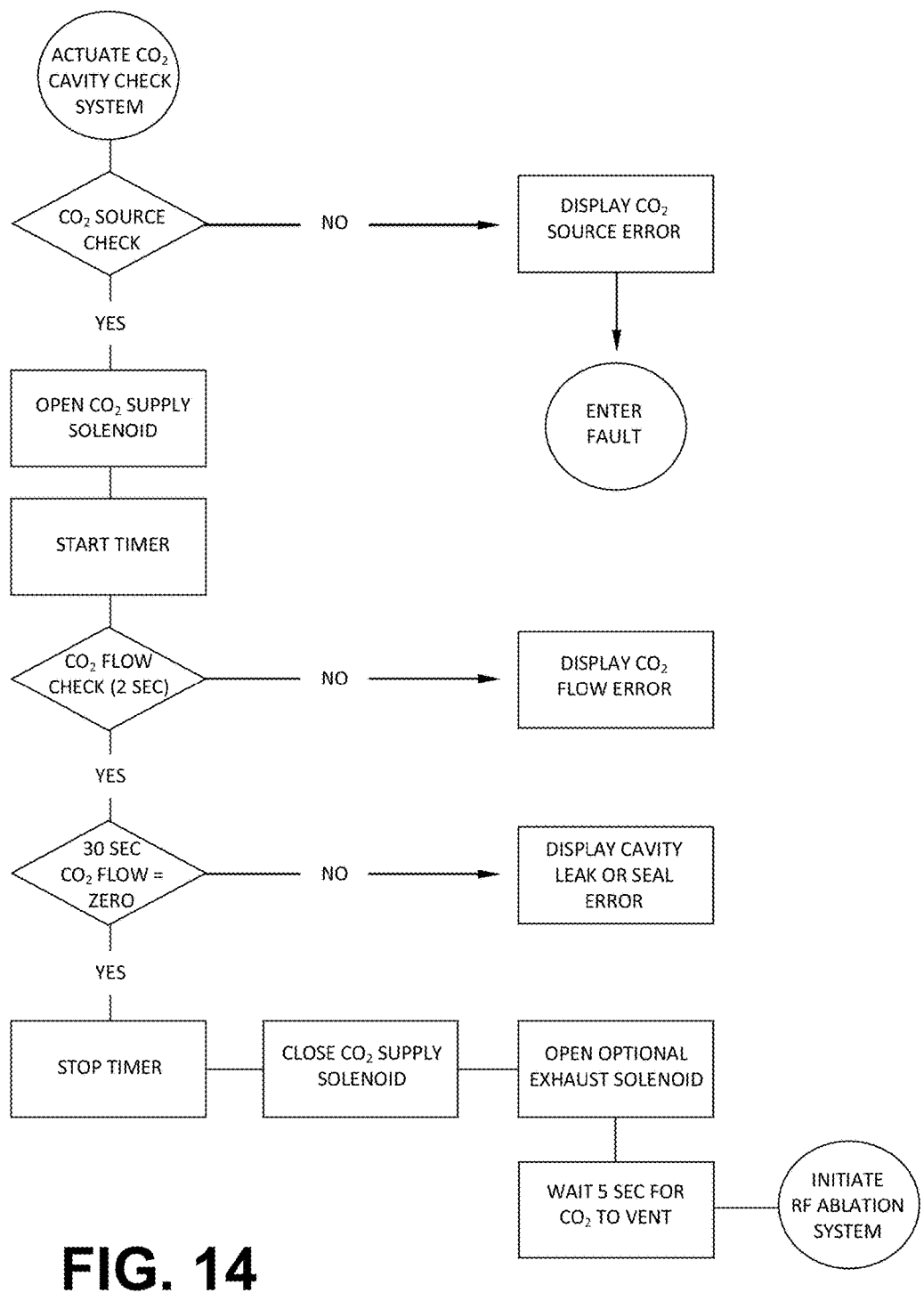
FIG. 14 represents a diagram indicating the steps of an algorithm for providing and monitoring a fluid flow into the patient's uterine cavity.

FIG. 14 depicts aspects of an algorithm used by controller 410 to accomplish a uterine cavity integrity check, with the first step comprising actuating a footswitch or hand switch. Upon actuation, a timer is initialized for 1 to 5 seconds to determine that a fluid source 405 is capable of providing a fluid flow, which can be checked by a pressure sensor between the source 405 and pressure regulator 422. If no flow is detected, an error signal is provided, such as a visual display signal on the control unit 135 (FIG. 1).

As can be understood from FIG. 14, after the fluid source 405 is checked, the controller opens the supply solenoid valve 450 and a timer is initialized for a 1 to 5 second test interval to insure fluid flows through the subsystem 420 of FIG. 13, with either or both a flow meter 440 or a pressure sensor. At the same time as valve 450 is opened, a timer is initialized for cavity integrity test interval of 30 seconds. The controller 410 monitors the flow meter 440 and provides a signal characterizing the uterine cavity as non-perforated if, at any time after the initial 5 second check interval and before the end of the timed-out period (e.g., the 30 second time-out), the flow rate drops below a threshold minimum rate, in one embodiment, to below 0.05 slpm. If the interval times out after 30 seconds and the flow rate does not drop below this threshold, then a signal is generated that characterizes that the uterine cavity is perforated. This signal also can indicate a failure of the occlusion balloon 225.

Referring to FIG. 14, in one embodiment, in response or otherwise as a result of the signal that the uterine cavity is not perforated, the controller 410 can automatically enable and activate the RF ablation system described above to perform an ablation procedure. The controller 410 can provide a time interval from 1 to 15 seconds to allow CO2 gas to vent from the uterine cavity 302 before activating RF energy delivery. In another embodiment, the endometrial ablation system may include the optional subsystem 275 for exhausting fluids or gas from the uterine cavity during an ablation treatment (see FIG. 4 and accompanying text). This subsystem 275 can be actuated to exhaust CO2 from the uterine cavity 302 which include opening solenoid valve 285 shown in FIG. 4.

The system can further include an override to repeat the cavity integrity check, for example, after evaluation and re-deployment of the occlusion balloon 225.

Figure 15:
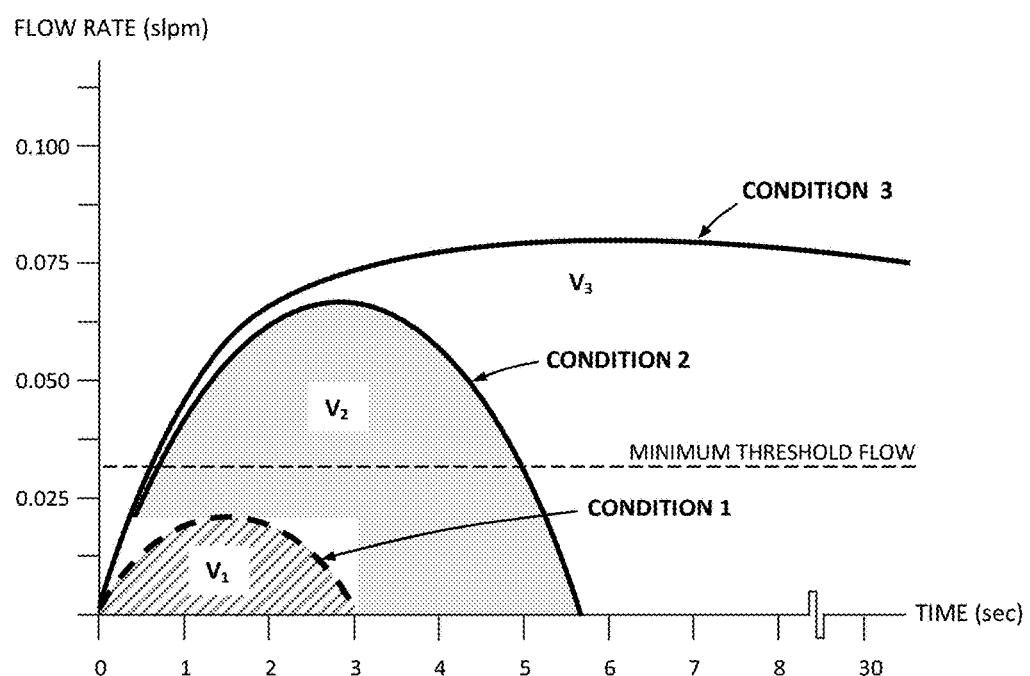
FIG. 15 is a chart illustrating gas flow rates into the uterine cavity over time that will result in three conditions to thereby characterize the uterine cavity as non-perforated or perforated.
Figure 16:
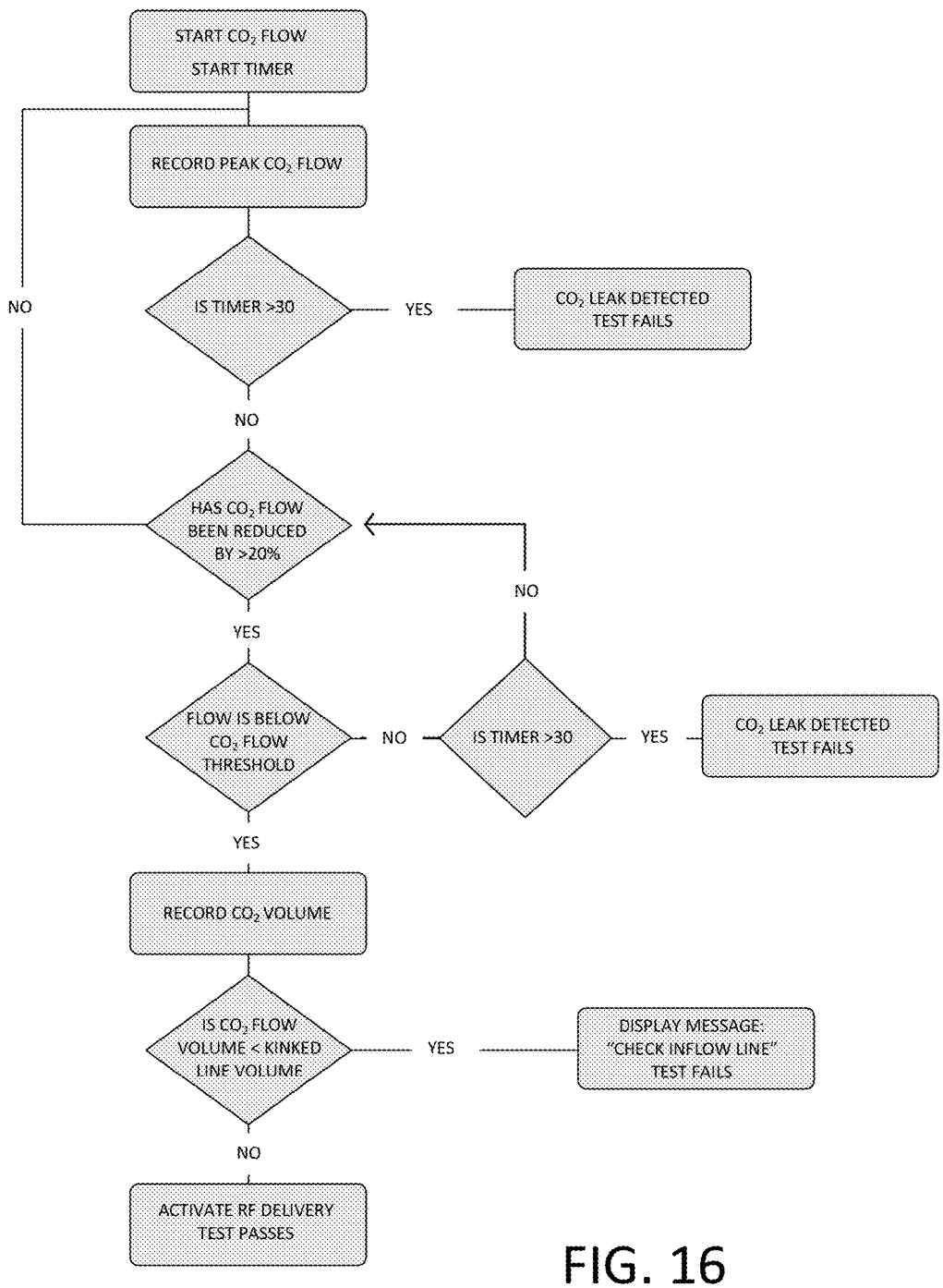
FIG. 16 represents a diagram indicating the steps of an algorithm for providing and monitoring a fluid flow related to the test method of FIG. 15.

FIGS. 15 and 16 represent another system and method for characterizing the uterine cavity as being non-perforated so as to safely permit an ablation procedure. This system and method utilizes variations in the algorithms that introduce a gas media fluid into the uterine cavity and thereafter measure the changes in flow rates in the gas media. The system again is configured to introduce a gas into the uterine cavity after deployment and expansion of an ablation device in the cavity. If the flow rate of the gas drops to approximately zero, this indicates that the uterine cavity is intact and not perforated. In the event the flow rate of the gas does not drop, there is likely a gas escaping from the uterine cavity 302 through a perforation in the uterine wall. Thus, the gas flow failing to drop may be an indication of a perforation.

FIG. 15 schematically illustrates three different conditions that may occur when operating the system, which indicate whether the system is functioning properly, and whether the uterine wall is non-perforated or perforated. In FIG. 15, the vertical axis indicates a gas flow rate measure in slpm (standard liters per minute), and the horizontal axis represents time in seconds. In one system variation, a gas source 405 such as a pressurized cartridge containing $CO_2$ is controlled by a controller 410, and the gas is introduced into the uterine cavity through a passageway in the device introducer sleeve 110 as described above (FIGS. 11-13). The controller 410 and flowmeter monitor flows from the device into the uterine cavity (FIG. 13). The initial flow rate can be in the range of 0.010 slpm to 0.20 slpm. In one aspect of the invention, a minimum flow rate has been found to be important as a system diagnostic check to insure gas flow is reaching the uterine cavity. Thus, FIG. 15 illustrates gas flow rate curve in a "condition 1" that may occur when the system fails in delivering gas through the passageways of the system. In one variation, the "condition 1" will be represented by a flow rate over time wherein the flow rate does not achieve a minimum threshold flow rate, which can be from 0.010 slpm to 0.050 slpm over a predetermined time interval. In one variation, the minimum flow rate is 0.035 slpm. The time interval can be from 1 second to 15 seconds. This "condition 1" as in FIG. 15 could occur, for example, if the gas supply tubing within the device were kinked or pinched which would then prevent gas flow through the system and into the uterine cavity. In a related variation that indicates system failure, a controller algorithm can calculate the volume of gas delivered, and if the volume is less than a threshold volume, then a system failure or fault can be determined. The gas volume $V_1$ is represented by the "area under the curve" in FIG. 15, which is a function of flow rate and time.

FIG. 15 further illustrates a flow rate curve in a "condition 2" which corresponds to an intact, non-perforated uterine cavity. As can be understood from a practical perspective, a gas flow into an intact uterine cavity at a set pressure from a low pressure source, for example within a range of 0.025 psi to 1.0 psi, would provide an increasing flow rate into the cavity until the cavity was filled with gas, and thereafter the flow rate would diminish to a very low or zero flow rate. Such a "condition 2" flow rate curve as in FIG. 15 further assumes that there is an adequate sealing mechanism in the cervical canal. Thus, if controller obtains flow rate data from the flowmeter indicating "condition 2", then the patient's uterus is non-perforated and is suitable for an ablation. In operation, the controller can look at various specific aspects and parameters of the flow rate curve of "condition 2" in FIG. 15 to determine that the uterine cavity integrity test has passed, wherein such parameters can comprise any single parameter or a combination of the following parameters: (i) the flow rate falling below a threshold rate, for example between 0.010-0.10 slpm; (ii) a change in rate of flow; (iii) a peak flow rate; (iii) the total gas volume $V_2$ delivered; (iv) an actual flow rate at a point in time compared to a peak flow rate; (v) a derivative of flow rate at a point in time, and (vi) any of the preceding parameters combined with a predetermined time interval. In one embodiment, a constant pressure (0.85 psi) gas is introduced and a minimum threshold flow is set at 0.035 slpm. A peak flow is calculated after a time interval of 2 to 15 seconds, and thereafter it is determined if the flow rate diminished by at least 10%, 20%, 30%, 40% or 50% over a time interval of less than 30 seconds.

FIG. 15 next illustrates a flow rate curve in "condition 3" which represents a gas flow when there is a perforated wall in a uterine cavity, which would allow the gas to escape into the abdominal cavity. In FIG. 15, a gas flow at a constant pressure is shown ramping up in flow rate until it levels off and may decline but not the rate of decline to may not go below a threshold value or may not decline a significant amount relative to a peak flow rate. Such a flow rate curve over time would indicate that the gas is leaking from the uterine cavity.

Now turning to FIG. 16, an algorithm diagram is shown that describe one variation in a method of operating a uterine cavity integrity test based on measuring gas flow rates over a selected time interval. At the top of the diagram, the physician actuates the system in which a valve 450 is opened to provide a $CO_2$ flow through the system (FIG. 14). The controller 410 provides a flow at a pressure, for example 0.85 psi. The actuation of the system also starts a timer wherein a first interval is 30 seconds or less. Over this 30-second interval, the controller records the peak flow rate which typically can occur within 2 to 10 seconds, then monitors the flow rate over the remainder of the 30 second interval and determined whether the flow rate drops 20% or more from the peak flow rate. Then, the controller additionally monitors whether the flow rate falls below a threshold value, for example 0.035 slpm. If these two conditions are met, the test indicates that there is no leakage of gas media from the uterine cavity. If the flow rates does not drop 20% from its peak with 30 seconds together with flow being below threshold value, then the test fails indicating a leak of gas from the uterine cavity. Thereafter, the diagram in FIG. 16, indicates one additional test which consists of calculating the volume of gas delivered and comparing the volume to the maximum volume within a kinked gas delivery line. If the delivered gas volume is less than the capacity of the gas delivery line, then the test fails and the signal on the controller can indicate this type of test failure. If the delivered gas volume is greater than the capacity of a gas delivery line, then the test passes. In one variation of the controller algorithm can then automatically actuate the delivery of RF energy in an ablation cycle. Alternatively, the controller can provide a signal that the test has passed, and the physician can manually actuate the RF ablation system.

Figure 17:
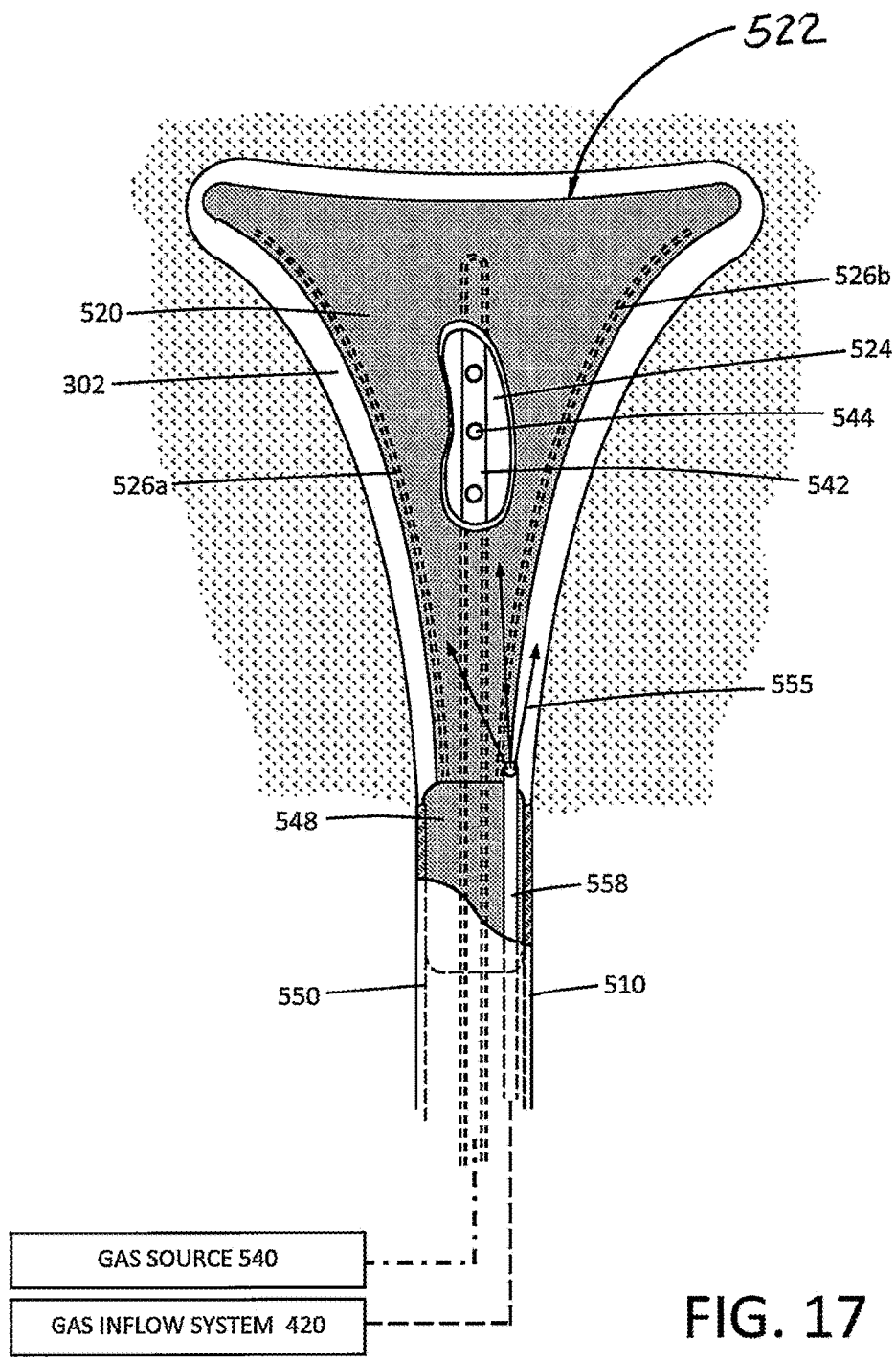
FIG. 17 is a schematic view of another system and method for providing and monitoring a fluid flow to characterize the integrity of a uterine cavity.

FIG. 17 schematically illustrates another system and method for characterizing integrity of the walls of a uterine cavity. As can be seen in FIG. 17. an introducer sleeve 510 carrying an expandable working end 520 is deployed in the uterine cavity 302. The working end includes a balloon-like member 522 with a fluid-tight interior chamber 524. In one embodiment, the working end 510 is expanded laterally by frame elements 526a and 526b, which is similar to previously described embodiments. In addition, a pressurized gas source 540 is actuated to provide an inflation gas thru interior sleeve 542 and ports 544 therein that further expands and opens the working end 520 transverse to opening forces applied by frame elements 526a and 526b. The inflation gas can comprise an argon gas that later is converted to a plasma as described previously. The inflation gas can pressurize the working end to a selected pressure ranging from 0.10 psi to 10 psi. In one variation, the pressure can be 0.50 psi.

As can be seen in FIG. 17, an expandable member 548 or balloon is expanded to prevent any gas flow outwardly through the bore 550 in introducer sleeve 510. Thereafter, a gas inflow system 410 similar to that of FIG. 13 is utilized to flow a gas source, such as $CO_2$ into the uterine cavity 302 (FIG. 17). In FIG. 17, the gas inflow is indicated by arrows 555 which can comprise an inflow at a predetermined pressure through passageway 558 as described above, and in one variation can be 0.85 psi. The test for uterine cavity integrity then can monitor one or more gas leakage parameters relating to the inflation gas in the interior chamber 524 of the working end 520. For example, the flow into the uterine cavity 302 will cause an outflow of gas from the interior chamber 524 through passageway 558 which can be measure by a flow meter, or the volume of gas outflow can be measured or the change in gas pressure can be measured. If there is no leak in the uterine cavity, the parameter of the inflation can in the interior chamber 524 will reach an equilibrium in relation to the $CO_2$ inflow into the cavity. If the inflation gas parameter does not reach an equilibrium, then the change in parameter (flow, volume or pressure) will indicate a leakage of gas from the uterine cavity through a perforation. In general, a method of characterizing the integrity of a patient's uterus comprises positioning a probe working end is a patient's uterine cavity, the working end comprising an inflated resilient structure, introducing a flow of a gas through the probe into a uterine cavity exterior about the exterior of the working end, and measuring a gas flow, gas volume or gas pressure parameter of the inflation media in the inflated resilient structure in response to the gas flow into the uterine cavity.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for characterizing a patient's uterus, said system comprising:
   a probe;
   means for introducing a flow of gas through the probe;
   means for measuring an inflow rate of the flow of gas through the probe when positioned in the uterus;
   means for comparing a measured peak flow with a measured subsequent flow rate through the probe to produce a comparison of the measured peak flow rate and the measured subsequent flow rate; and
   means for determining whether the uterus cavity is perforated based at least in part on the comparison of the peak and subsequent flow rates.

2. A system as in claim 1, wherein the probe is adapted for transcervical introduction to the uterus.

3. A system as in claim 1, wherein the gas introducing means is adapted to deliver the gas at a pre-determined constant pressure.

4. A system as in claim 3, wherein the gas introducing means is adapted to introduce the gas at a pressure in the range from 0.025 psi to 1 psi.

5. A system as in claim 3, wherein the gas introducing means is adapted to deliver gas at a pre-determined initial flow rate.

6. A system as in claim 5, wherein the initial flow rate is in the range from 0.05 slpm to 0.2 slpm.

7. A system as in claim 5, wherein the determining means detects when the initial flow rate drops by at least 10%, 20%, 30%, 40%, or 50% of the initial flow rate.

8. A system as in claim 5, wherein the determining means detects when the initial flow rate drops to a value in the range from 0.01 slpm to 0.1 slpm.

\* \* \* \* \*